US012144623B2

United States Patent
Dehennis et al.

(10) Patent No.: US 12,144,623 B2
(45) Date of Patent: *Nov. 19, 2024

(54) DETECTING AND CORRECTING FOR CHANGES TO AN ANALYTE INDICATOR

(71) Applicant: Senseonics, Incorporated, Germantown, MD (US)

(72) Inventors: Andrew Dehennis, Germantown, MD (US); Mark Mortellaro, Germantown, MD (US); Abhi Chavan, Germantown, MD (US); Venkata Velvadapu, Germantown, MD (US); Philip Huffstetler, Germantown, MD (US); Tina HyunJung Kim, Germantown, MD (US); James Masciotti, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/061,334

(22) Filed: Dec. 2, 2022

(65) Prior Publication Data

US 2023/0103609 A1    Apr. 6, 2023

Related U.S. Application Data

(63) Continuation of application No. 17/092,830, filed on Nov. 9, 2020, now Pat. No. 11,517,230, which is a
(Continued)

(51) Int. Cl.
*A61B 5/1495* (2006.01)
*A61B 5/00* (2006.01)
(Continued)

(52) U.S. Cl.
CPC .......... *A61B 5/1495* (2013.01); *A61B 5/0031* (2013.01); *A61B 5/076* (2013.01);
(Continued)

(58) Field of Classification Search
CPC . A61B 5/1455; A61B 5/14556; A61B 5/1495; A61B 5/14532; A61B 5/1459;
(Continued)

(56) References Cited

U.S. PATENT DOCUMENTS 6,002,954 A    12/1999  Van Antwerp et al.
6,330,464 B1   12/2001  Colvin, Jr. et al.
(Continued)

FOREIGN PATENT DOCUMENTS

| EP | 2779900 B1 | 9/2015 |
|---|---|---|
| WO | 2016/154034 A1 | 9/2016 |
| WO | 2017/105927 A1 | 6/2017 |

OTHER PUBLICATIONS

Mortellaro, Mark et al., "Performance characterization of an abiotic and fluorescent-based continuous glucose monitoring system in patients with type 1 diabetes," Biosensors and Bioelectronics, vol. 61, pp. 227-231 (2014).
(Continued)

*Primary Examiner* — Eric F Winakur
(74) *Attorney, Agent, or Firm* — Rothwell, Figg, Ernst & Manbeck, P.C.

(57) ABSTRACT

A sensor, system, and method for detecting and correcting for changes to an analyte indicator of an analyte sensor. The analyte indicator may be configured to exhibit a first detectable property that varies in accordance with an analyte concentration and an extent to which the analyte indicator has degraded. The analyte sensor may also include a degradation indicator configured to exhibit a second detectable property that varies in accordance with an extent to which
(Continued)

the degradation indicator has degraded. The analyte sensor may generate (i) an analyte measurement based on the first detectable property exhibited by the analyte indicator and (ii) a degradation measurement based on the second detectable property exhibited by the degradation indicator. The analyte sensor may be part of a system that also includes a transceiver. The transceiver may use the analyte and degradation measurements to calculate an analyte level.

18 Claims, 13 Drawing Sheets

Related U.S. Application Data continuation of application No. 15/957,604, filed on Apr. 19, 2018, now Pat. No. 10,827,962.

(60) Provisional application No. 62/487,289, filed on Apr. 19, 2017.

(51) Int. Cl.
| | | |
|---|---|---|
| A61B 5/07 | (2006.01) | |
| A61B 5/145 | (2006.01) | |
| A61B 5/1455 | (2006.01) | |
| A61B 5/1459 | (2006.01) | |
| A61B 5/1473 | (2006.01) | |

(52) U.S. Cl.
CPC ...... *A61B 5/14532* (2013.01); *A61B 5/14556* (2013.01); *A61B 5/1459* (2013.01); *A61B 5/14546* (2013.01); *A61B 5/1473* (2013.01); *A61B 2560/0219* (2013.01); *A61B 2560/0266* (2013.01)

(58) Field of Classification Search
CPC . A61B 5/14546; A61B 5/6846; A61B 5/6861; A61B 5/7271; A61B 5/0031
See application file for complete search history.

(56) References Cited

U.S. PATENT DOCUMENTS

| | | |
|---|---|---|
| 7,060,503 B2 | 6/2006 | Colvin, Jr. |
| 8,073,548 B2 | 12/2011 | Colvin, Jr. et al. |
| 8,143,068 B2 | 3/2012 | Colvin, Jr. et al. |
| 9,414,775 B2 | 8/2016 | Colvin, Jr. et al. |
| 9,427,181 B2 | 8/2016 | Emken et al. |
| 9,427,182 B2 | 8/2016 | Emken et al. |
| 9,611,504 B2 | 4/2017 | Petrich et al. |
| 9,693,714 B2 | 7/2017 | DeHennis et al. |
| 9,778,190 B2 | 10/2017 | Huffstetler et al. |
| 2008/0188725 A1 | 8/2008 | Markle et al. |
| 2011/0081727 A1 | 4/2011 | Colvin, Jr. et al. |
| 2012/0238842 A1 | 9/2012 | Colvin, Jr. et al. |
| 2012/0265035 A1 | 10/2012 | Bohm et al. |
| 2013/0241745 A1 | 9/2013 | Colvin, Jr. et al. |
| 2014/0018644 A1 | 1/2014 | Colvin, Jr. et al. |
| 2014/0088383 A1 | 3/2014 | Colvin, Jr. et al. |
| 2014/0128694 A1 | 5/2014 | Gallant et al. |
| 2016/0312033 A1 | 10/2016 | Yang et al. |
| 2017/0049371 A1 | 2/2017 | Emken et al. |
| 2022/0287597 A1 | 9/2022 | DeHennis et al. |

OTHER PUBLICATIONS

Bryan C Dickinson et al., "Preparation and use of MitoPY1 for imaging hydrogen peroxide in mitochondria of live cells," Nat Protoc. Jun. 2013 ; 8(6): 1249-1259. doi:10.1038/nprot.2013.064.

DETECTING AND CORRECTING FOR CHANGES TO AN ANALYTE INDICATOR

CROSS-REFERENCE TO RELATED APPLICATION

This application is a continuation of U.S. application Ser. No. 17/092,830, filed on Nov. 9, 2020, which is a continuation of U.S. application Ser. No. 15/957,604, filed on Apr. 19, 2018, now U.S. Pat. No. 10,827,962, which claims the benefit of priority to U.S. Provisional Application Ser. No. 62/487,289, filed on Apr. 19, 2017, each of which are incorporated herein by reference in their entireties.

BACKGROUND

Field of Invention

The present invention relates generally to detecting and correcting for changes to an analyte indicator. Specifically, the present invention may relate to detecting and correcting for oxidation-induced degradation of an analyte indicator in an analyte monitoring system.

Discussion of the Background

Analyte monitoring systems may be used to monitor analyte levels, such as analyte concentrations (e.g., glucose concentrations). One type of analyte monitoring system is a continuous analyte monitoring system. A continuous analyte monitoring system measures analyte levels throughout the day and can be very useful in the management of diseases, such as diabetes.

Some analyte monitoring systems include an analyte sensor, which may be implanted (fully or partially) in an animal and may include an analyte indicator. The analyte sensor may lose sensitivity while implanted in the animal as a result of changes in sensitivity parameters (e.g., calibration constants). The changes in sensitivity parameters may be due to, for example, degradation of the analyte indicator. The degradation may be caused by, for example, oxidation of the analyte indicator induced by cellular generated reactive oxygen species (ROS). See, e.g., U.S. Pat. Nos. 8,143,068, 9,427,181, and U.S. Patent Application Publication No. 2012/0238842, each of which are incorporated by reference herein in their entireties. The rate in vivo sensitivity loss can be reduced by, for example, using oxidation resistant indicator molecules, integrating catalytic protection, and/or using a membrane that catalyzes degradation of reactive oxygen species (ROS). However, the reducing the rate of in vivo sensitivity loss does not completely prevent sensitivity loss. The gradual change in sensitivity parameters over time may negatively affect analyte sensing accuracy and may necessitate re-calibrations using reference analyte measurements (e.g., self-monitoring blood glucose measurements), which may be uncomfortable and/or otherwise undesirable for a user.

SUMMARY

The present invention overcomes the disadvantages of prior systems by providing an analyte monitoring system capable of detecting changes to an analyte indicator and correcting for the detected changes. In contrast with prior art systems that can only correct for changes to an analyte indicator at the time of a re-calibration that uses a reference analyte measurement, the analyte monitoring system may provide, among other advantages, the ability to correct for changes to the analyte indicator without the need for a reference analyte measurement. In some embodiments, the analyte monitoring system may include an analyte sensor that measures changes to the analyte indicator indirectly using a degradation indicator, which may by sensitive to degradation by reactive oxygen species (ROS) but not sensitive to the analyte. In some embodiments, the degradation indicator may have optical properties that change with extent of oxidation and may be used as a reference dye for measuring and correcting for extent of oxidation of the analyte indicator. In some embodiments, the analyte monitoring system may correct for changes in the analyte indicator using an empiric correlation established through laboratory testing.

One aspect of the invention may provide an analyte sensor for measurement of an analyte in a medium within a living animal. The analyte sensor may include an analyte indicator, a degradation indicator, and sensor elements. The analyte indicator may be configured to exhibit a first detectable property that varies in accordance with (i) an amount or concentration of the analyte in the medium and (ii) an extent to which the analyte indicator has degraded. The degradation indicator may be configured to exhibit a second detectable property that varies in accordance with an extent to which the degradation indicator has degraded. The extent to which the degradation indicator has degraded may correspond to the extent to which the analyte indicator has degraded. The sensor elements may be configured to generate (i) an analyte measurement based on the first detectable property exhibited by the analyte indicator and (ii) a degradation measurement based on the second detectable property exhibited by the degradation indicator.

In some embodiments, the extent to which the degradation indicator has degraded may be proportional to the extent to which the analyte indicator has degraded. In some embodiments, degradation to the analyte indicator may include reactive oxidation species (ROS)-induced oxidation, and degradation to the degradation indicator includes ROS-induced oxidation. In some embodiments, the analyte indicator may be a phenylboronic-based analyte indicator. In some embodiments, the degradation indicator may be a phenylboronic-based degradation indicator.

In some embodiments, the analyte sensor may further include an indicator element comprising the analyte indicator and the degradation indicator. In some embodiments, the analyte indicator may include analyte indicator molecules distributed throughout the indicator element, and the degradation indicator may include degradation indicator molecules distributed throughout the indicator element. In some embodiments, the second detectable property does not vary in accordance with the amount or concentration of the analyte in the medium.

In some embodiments, the sensor elements may include a first light source and a first photodetector. The first light source may be configured to emit first excitation light to the analyte indicator. The first photodetector configured to receive first emission light emitted by the analyte indicator and output the analyte measurement. The analyte measurement may be indicative of an amount of first emission light received by the first photodetector. In some embodiments, the sensor elements may include a second light source and a second photodetector. The second light source may be configured to emit second excitation light to the degradation indicator. The second photodetector may be configured to receive second emission light emitted by the degradation indicator and output the degradation measurement. The degradation measurement may be indicative of an amount of second emission light received by the second photodetector. In some embodiments, the first photodetector may be configured to receive second excitation light reflected from the indicator element and output a first reference signal indicative of an amount of reflected second excitation light received by the first photodetector. In some embodiments, the sensor elements may include a third photodetector configured to receive first excitation light reflected from the indicator element and output a second reference signal indicative of an amount of reflected first excitation light received by the third photodetector.

Another aspect of the invention may provide a method including using an analyte indicator of an analyte sensor to measure an amount or concentration of an analyte in a medium. The method may include using a degradation indicator of the analyte sensor to measure an extent to which the degradation indicator has degraded. The method may include using a sensor interface device of a transceiver to receive from the analyte sensor an analyte measurement indicative of the amount or concentration of the analyte in the medium. The method may include using the sensor interface device of the transceiver to receive from the analyte sensor a degradation measurement indicative of the extent to which the degradation indicator has degraded. The method may include using a controller of the transceiver to calculate an extent to which the analyte indicator of the analyte sensor has degraded based at least on the received degradation measurement. The method may include using the controller of the transceiver to adjust a conversion function based on the calculated extent to which the analyte indicator has degraded. The method may include using the controller of the transceiver to calculate an analyte level using the adjusted conversion function and the received analyte measurement. The method may include displaying the calculated analyte level.

Still another aspect of the invention may provide an analyte monitoring system including an analyte sensor and a transceiver. The analyte sensor may include an analyte indicator, a degradation indicator, sensor elements, and a transceiver interface device. The analyte indicator may be configured to exhibit a first detectable property that varies in accordance with (i) an amount or concentration of an analyte in a medium and (ii) an extent to which the analyte indicator has degraded. The degradation indicator may be configured to exhibit a second detectable property that varies in accordance with an extent to which the degradation indicator has degraded. The sensor elements may be configured to generate (i) an analyte measurement based on the first detectable property exhibited by the analyte indicator and (ii) a degradation measurement based on the second detectable property exhibited by the degradation indicator. The transceiver may include a sensor interface device and a controller. The controller may be configured to: (i) receive the analyte measurement from the analyte sensor via the transceiver interface device of the analyte sensor and the sensor interface device; (ii) receive the degradation measurement from the analyte sensor via the transceiver interface device of the analyte sensor and the sensor interface device; (iii) calculate an extent to which the analyte indicator of the analyte sensor has degraded based at least on the received degradation measurement; (iv) adjust a conversion function based on the calculated extent to which the analyte indicator has degraded; and (v) calculate an analyte level using the adjusted conversion function and the received analyte measurement.

In some embodiments, the analyte sensor may further include an indicator element, and the indicator element may include the analyte indicator and the degradation indicator. In some embodiments, the second detectable property does not vary in accordance with the amount or concentration of the analyte in the medium.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
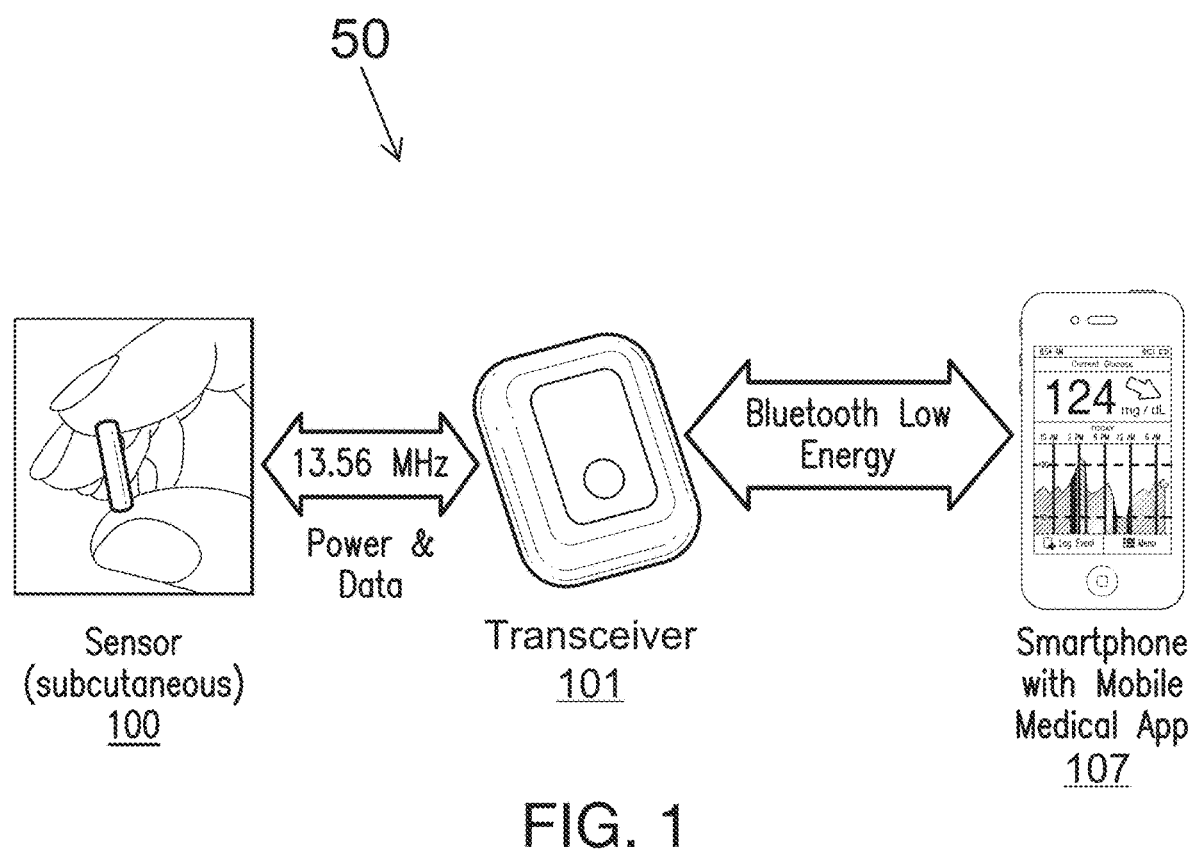
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 107. In some embodiments, the analyte sensor 100 may be a small, fully subcutaneously implantable sensor that measures the amount or concentration of an analyte (e.g., glucose) in a medium (e.g., interstitial fluid) of a living animal (e.g., a living human). However, this is not required, and, in some alternative embodiments, the analyte sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor 100 to initiate and receive the measurements (e.g., via near field communication (NFC)). However, this is not required, and, in some alternative embodiments, the transceiver 101 may power and/or communicate with the analyte sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte measurements) wirelessly (e.g., via a Bluetooth™ communication standard such as, for example and without limitation Bluetooth Low Energy) to a hand held application running on a display device 107 (e.g., smartphone).

Figure 2:
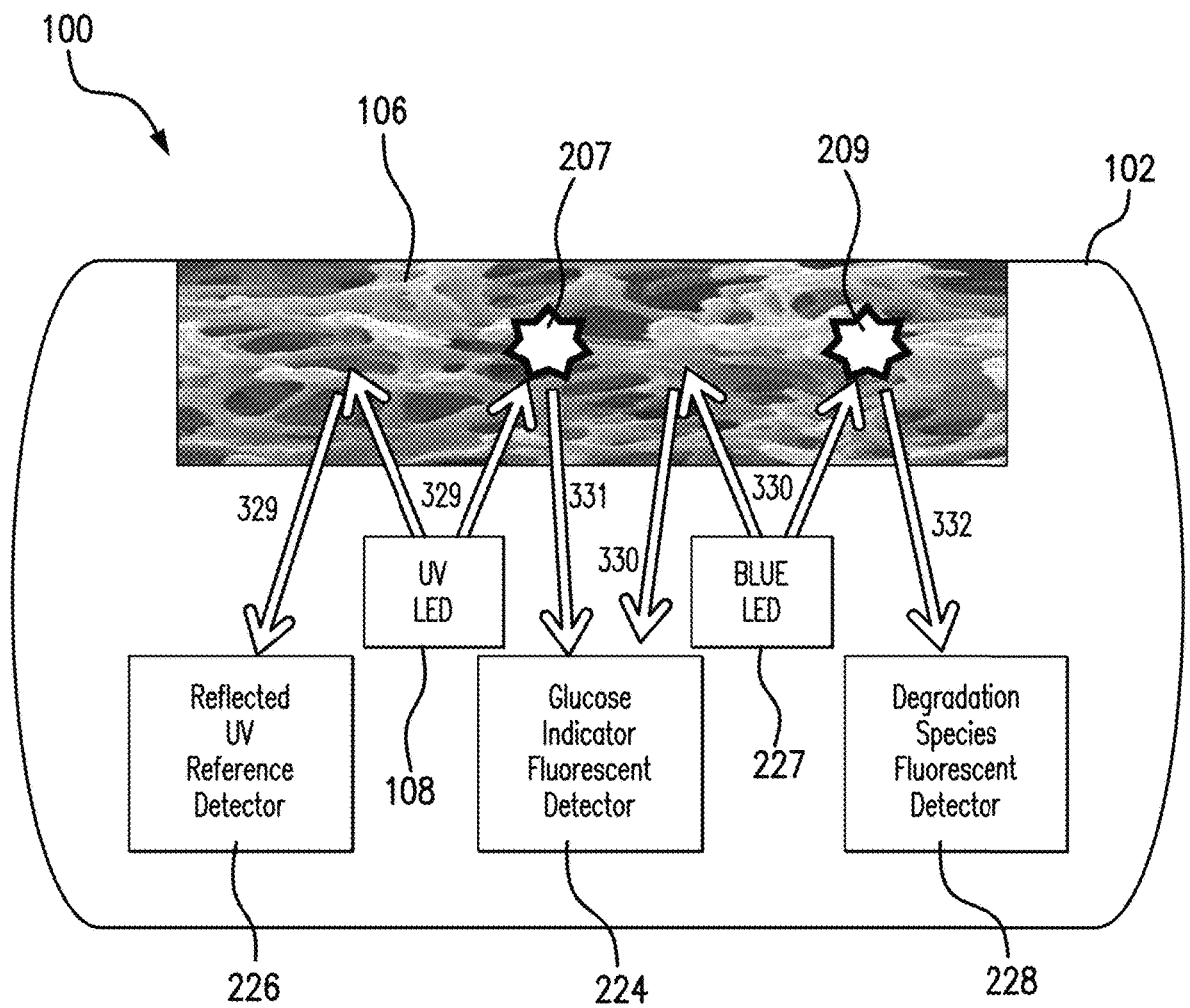
FIG. 2 is a schematic view illustrating an analyte sensor embodying aspects of the present invention.
Figure 3:
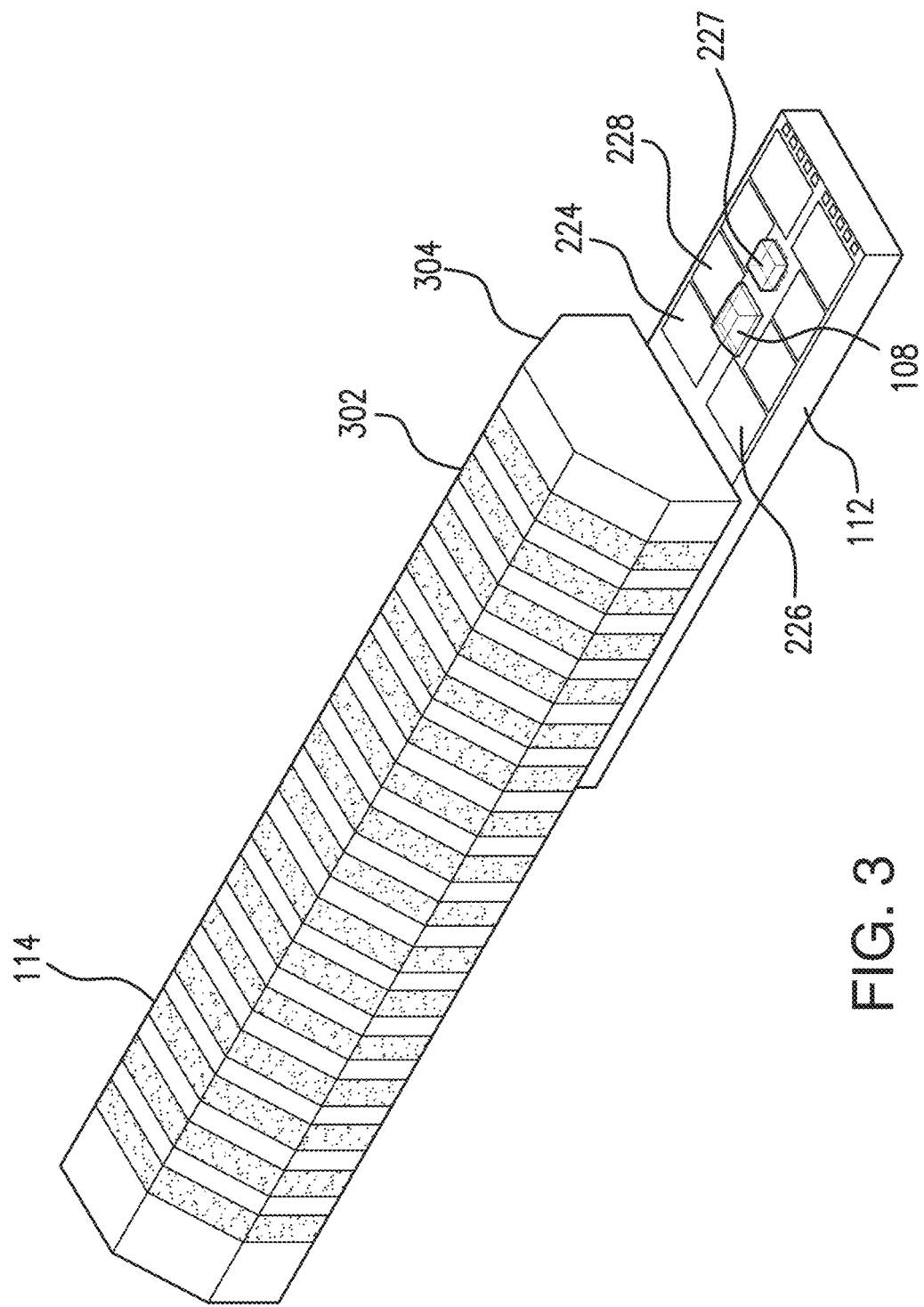
FIG. 3 is a perspective view illustrating elements of an analyte sensor embodying aspects of the present invention.
Figure 4:
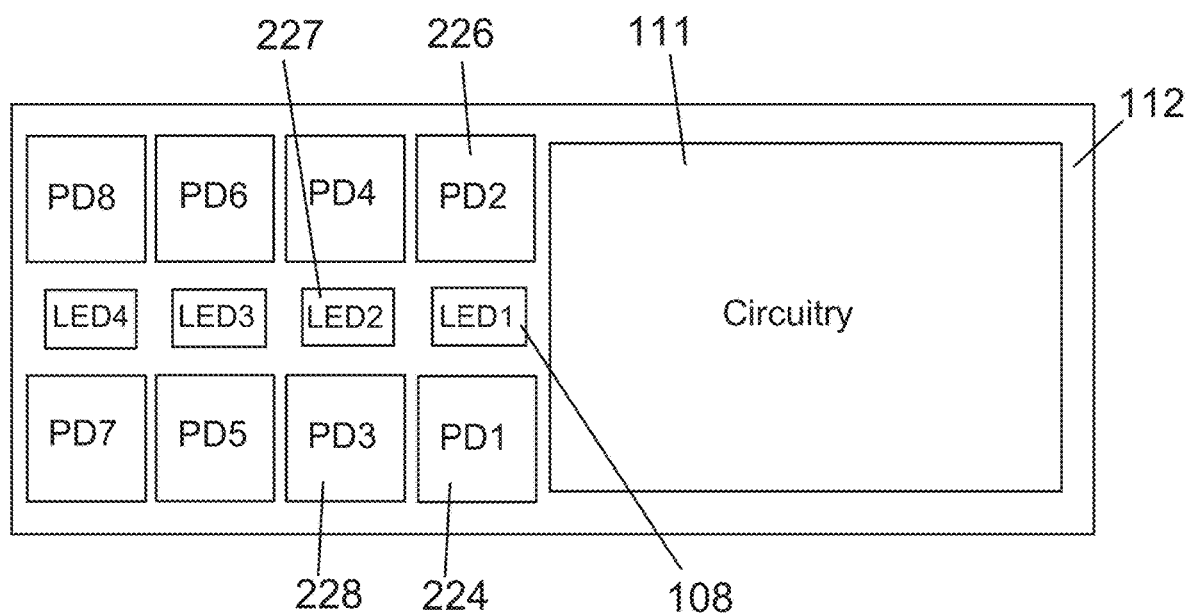
FIG. 4 is a schematic view illustrating the layout of a semiconductor substrate of an analyte sensor embodying aspects of the present invention.

FIG. 2 is a schematic view illustrating of an analyte sensor 100 embodying aspects of the present invention, and FIG. 3 is a perspective view illustrating elements of an analyte sensor 100 embodying aspects of the present invention. In some embodiments, the analyte sensor 100 may detect the presence, amount, and/or concentration of an analyte (e.g., glucose, oxygen, cardiac markers, low-density lipoprotein (LDL), high-density lipoprotein (HDL), or triglycerides). In some non-limiting embodiments, the analyte sensor 100 may be optical sensors (e.g., fluorometers). In some embodiments, the analyte sensor 100 may be chemical or biochemical sensors. In some embodiments, the analyte sensor 100 may be a radio frequency identification (RFID) device. The analyte sensor 100 may be powered by a radio frequency (RF) signal from the external transceiver 101.

The analyte sensor 100 may communicate with the external transceiver 101. The transceiver 101 may be an electronic device that communicates with the analyte sensor 100 to power the analyte sensor 100 and/or receive measurement data (e.g., photodetector and/or temperature sensor readings) from the analyte sensor 100. The measurement data may include one or more readings from one or more photodetectors of the analyte sensor 100 and/or one or more readings from one or more temperature sensors of the analyte sensor 100. In some embodiments, the transceiver 101 may calculate analyte concentrations from the measurement data received from the analyte sensor 100. However, it is not required that the transceiver 101 perform the analyte concentration calculations itself, and, in some alternative embodiments, the transceiver 101 may instead convey/relay the measurement data received from the analyte sensor 100 to another device for calculation of analyte concentrations. In other alternative embodiments, the analyte sensor 100 may perform the analyte concentration calculations.

In some embodiments (e.g., embodiments in which the analyte sensor 100 is a fully implantable sensing system), the transceiver 101 may implement a passive telemetry for communicating with the implantable analyte sensor 100 via an inductive magnetic link for power and/or data transfer. In some embodiments, as shown in FIG. 3, the analyte sensor 100 may include an inductive element 114, which may be, for example, a ferrite based micro-antenna. In some embodiments, as shown in FIG. 3, the inductive element 114 may include a conductor 302 in the form of a coil and a magnetic core 304. In some non-limiting embodiments, the core 304 may be, for example and without limitation, a ferrite core. In some embodiments, the inductive element 114 may be connected to analyte detection circuitry of the analyte sensor 100. For example, in some embodiments, where the analyte sensor 100 is an optical sensors, the inductive element 114 may be connected to micro-fluorimeter circuitry (e.g., an application specification integrated circuit (ASIC)) and a related optical detection system of the analyte sensor 100. In some embodiments, the analyte sensor 100 may not include a battery, and, as a result, the analyte sensor 100 may rely on the transceiver 101 to provide power for the analyte sensor 100 of the sensor system 105 and a data link to convey analyte-related data from the analyte sensor 100 to transceiver 101.

In some non-limiting embodiments, the analyte sensor 100 may be a passive, fully implantable multisite sensing system having a small size. For an analyte sensor 100 that is a fully implantable sensing system having no battery power source, the transceiver 101 may provide energy to run the analyte sensor 100 via a magnetic field. In some embodiments, the magnetic transceiver-sensing system link can be considered as "weakly coupled transformer" type. The magnetic transceiver-sensing system link may provide energy and a link for data transfer using amplitude modulation (AM). Although in some embodiments, data transfer is carried out using AM, in alternative embodiments, other types of modulation may be used. The magnetic transceiver-sensor link may have a low efficiency of power transfer and, therefore, may require relatively high power amplifier to energize the analyte sensor 100 at longer distances. In some non-limiting embodiments, the transceiver 101 and analyte sensor 100 may communicate using near field communication (e.g., at a frequency of 13.56 MHz, which can achieve high penetration through the skin and is a medically approved frequency band) for power transfer. However, this is not required, and, in other embodiments, different frequencies may be used for powering and communicating with the analyte sensor 100.

Figure 7:
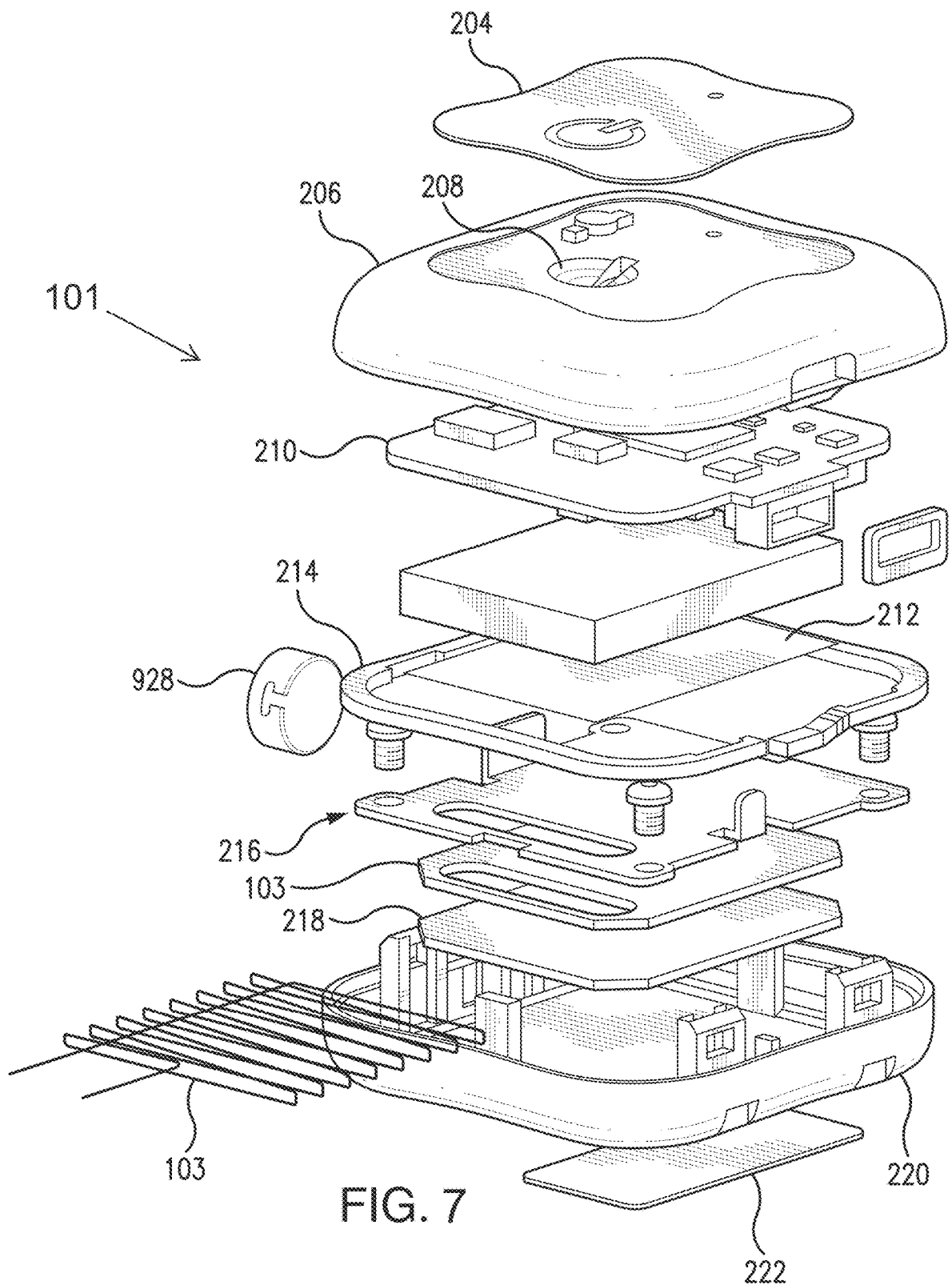
FIG. 7 is an exploded, perspective view of a transceiver embodying aspects of the invention.

In some embodiments, as shown in FIG. 7, the transceiver 101 may include an inductive element 103, such as, for example, a coil. The transceiver 101 may generate an electromagnetic wave or electrodynamic field (e.g., by using a coil 103) to induce a current in an inductive element 114 of the analyte sensor 100, which powers the analyte sensor 100. The transceiver 101 may also convey data (e.g., commands) to the analyte sensor 100. For example, in a non-limiting embodiment, the transceiver 101 may convey data by modulating the electromagnetic wave used to power the analyte sensor 100 (e.g., by modulating the current flowing through a coil of the transceiver 101). The modulation in the electromagnetic wave generated by the transceiver 101 may be detected/extracted by the analyte sensor 100. Moreover, the transceiver 101 may receive data (e.g., measurement information) from the analyte sensor 100. For example, in a non-limiting embodiment, the transceiver 101 may receive data by detecting modulations in the electromagnetic wave generated by the analyte sensor 100, e.g., by detecting modulations in the current flowing through the coil 103 of the transceiver 101.

In some non-limiting embodiments, as illustrated in FIG. 2, the analyte sensor 100 may include a sensor housing 102 (i.e., body, shell, capsule, or encasement), which may be rigid and biocompatible. In one non-limiting embodiment, the sensor housing 102 may be a silicon tube. However, this is not required, and, in other embodiments, different materials and/or shapes may be used for the sensor housing 102. In some embodiments, the analyte sensor 100 may include a transmissive optical cavity. In some non-limiting embodiments, the transmissive optical cavity may be formed from a suitable, optically transmissive polymer material, such as, for example, acrylic polymers (e.g., polymethylmethacrylate (PMMA)). However, this is not required, and, in other embodiments, different materials may be used for the transmissive optical cavity.

In some embodiments, as shown in FIG. 2, the analyte sensor 100 may include an indicator element 106, such as, for example, a polymer graft or hydrogel coated, diffused, adhered, embedded, or grown on or in at least a portion of the exterior surface of the sensor housing 102. In some non-limiting embodiments, the sensor housing 102 may include one or more cutouts or recesses, and the indicator elements 106 may be located (partially or entirely) in the cutouts or recesses. In some embodiments, the indicator element 106 may be porous and may allow the analyte (e.g., glucose) in a medium (e.g., interstitial fluid) to diffuse into the indicator element 106.

In some embodiments, the indicator element 106 (e.g., polymer graft or hydrogel) of the sensor 100 may include one or more of an analyte indicator 207 and a degradation indicator 209. In some embodiments, the analyte indicator 207 may exhibit one or more detectable properties (e.g., optical properties) that vary in accordance with (i) the amount or concentration of the analyte in proximity to the indicator element 106 and (ii) changes to the analyte indicator 207. In some embodiments, the changes to the analyte indicator 207 may comprise the extent to which the analyte indicator 207 has degraded. In some non-limiting embodiments, the degradation may be (at least in part) ROS-induced oxidation. In some embodiments, the analyte indicator 207 may include one or more analyte indicator molecules (e.g., fluorescent analyte indicator molecules), which may be distributed throughout the indicator element 106. In some non-limiting embodiments, the analyte indicator 207 may be a phenylboronic-based analyte indicator. However, a phenylboronic-based analyte indicator is not required, and, in some alternative embodiments, the analyte sensor 100 may include a different analyte indicator, such as, for example and without limitation, glucose oxidase-based indicators, glucose dehydrogenase-based indicators, and glucose binding protein-based indicators.

In some embodiments, the degradation indicator 209 may exhibit one or more detectable properties (e.g., optical properties) that vary in accordance with changes to the degradation indicator 209. In some embodiments, the degradation indicator 209 is not sensitive to the amount of concentration of the analyte in proximity to the indicator element 106. That is, in some embodiments, the one or more detectable properties exhibited by the degradation indicator 209 do not vary in accordance with the amount or concentration of the analyte in proximity to the indicator element 106. However, this is not required, and, in some alternative embodiments, the one or more detectable properties exhibited by the degradation indicator 209 may vary in accordance with the amount or concentration of the analyte in proximity to the indicator element 106.

In some embodiments, the changes to the degradation indicator 209 may comprise the extent to which the degradation indicator 209 has degraded. In some embodiments, the degradation may be (at least in part) ROS-induced oxidation. In some embodiments, the degradation indicator 209 may include one or more degradation indicator molecules (e.g., fluorescent degradation indicator molecules), which may be distributed throughout the indicator element 106. In some non-limiting embodiments, the degradation indicator 209 may be a phenylboronic-based degradation indicator. However, a phenylboronic-based degradation indicator is not required, and, in some alternative embodiments, the analyte sensor 100 may include a different degradation indicator, such as, for example and without limitation, amplex red-based degradation indicators, dichlorodihydrofluorescein-based indicators, dihydrorhodamine-based indicators, and scopoletin-based degradation indicators.

In some non-limiting embodiments, a degradation indicator molecule may be a fluorescent probe compound having a wavelength of excitation between about 450 nm and about 550 nm, a Stokes shift between about 500 nm and about 650 nm, and a half-life of between about 50 days and about 150 days. In some non-limiting embodiments, a degradation indicator molecule may be a compound of formula I:

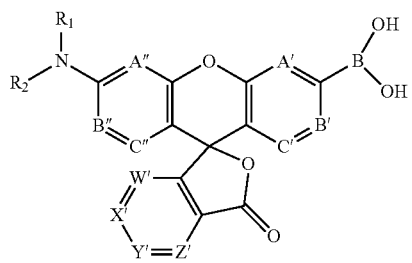

wherein A", B", C", A', B', C', W', X, Y', and Z' represent —CH, wherein the hydrogen may optionally and independently be substituted with an alkyl group, $R_1$ and $R_2$ are independently selected from one or more vinyl groups, alkyl vinyl groups, acrylamide groups, methacrylamide groups, or other polymerizable groups.

Exemplary and non-limiting compounds include the following:

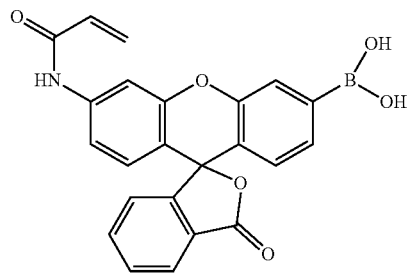

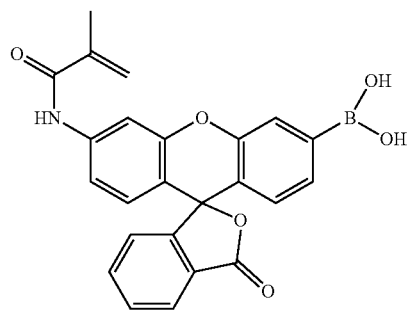

-continued

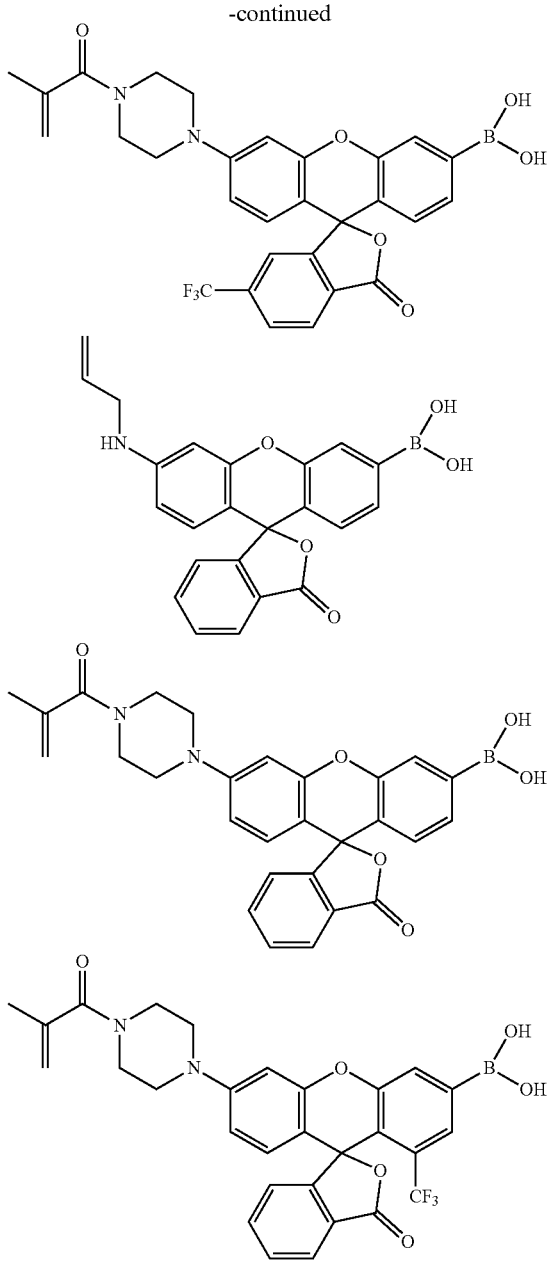

Compounds may be synthesized using the synthetic techniques known in the art such as in "Preparation and use of MitoPY1 for imaging hydrogen peroxide in mitochondria of live cells," Dickinson, et al. Nat Protoc. 2013 June; 8(6): 1249-1259 and U.S. pre-grant publication number US2016/0312033 (application Ser. No. 15/135,788, Yang et al., Oct. 27, 2016), the disclosures of which are incorporated herein by reference in their entireties.

In some alternative embodiments, the molecules of the degradation indicator 209 may be a compound having a different formula having a wavelength of excitation between about 450 nm and about 550 nm, a Stokes shift between about 500 nm and about 650 nm, and a half-life of between about 50 days and about 150 days.

Figure 10:
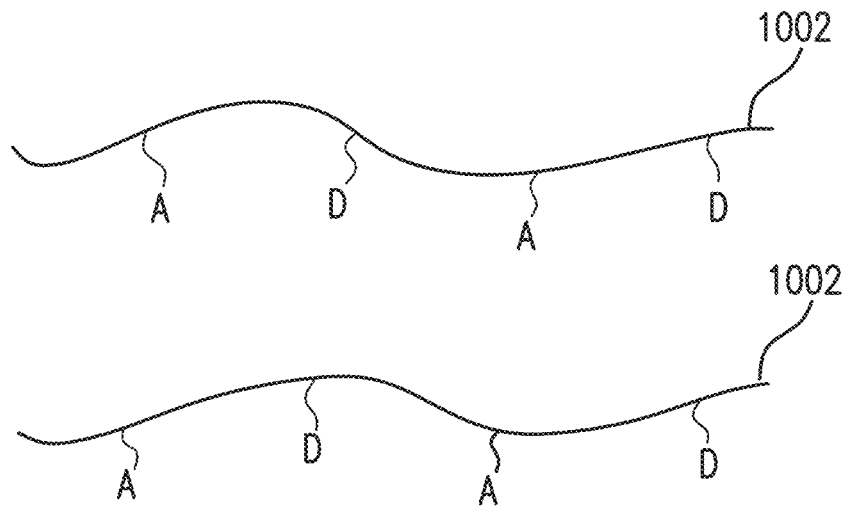
FIGS. 10-12 are schematic diagrams illustrating non-limiting examples of structures of indicator elements 106 embodying aspects of the present invention.
Figure 11:
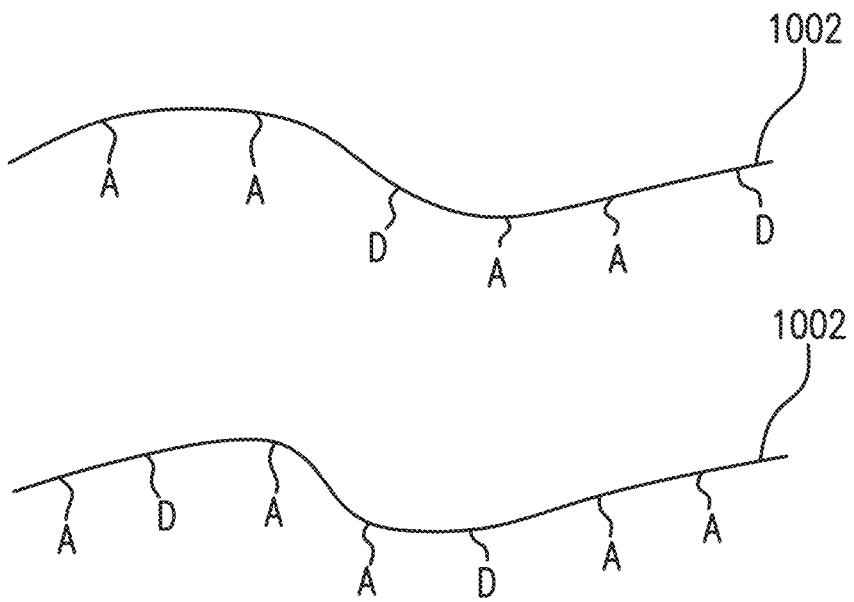
Figure 12:
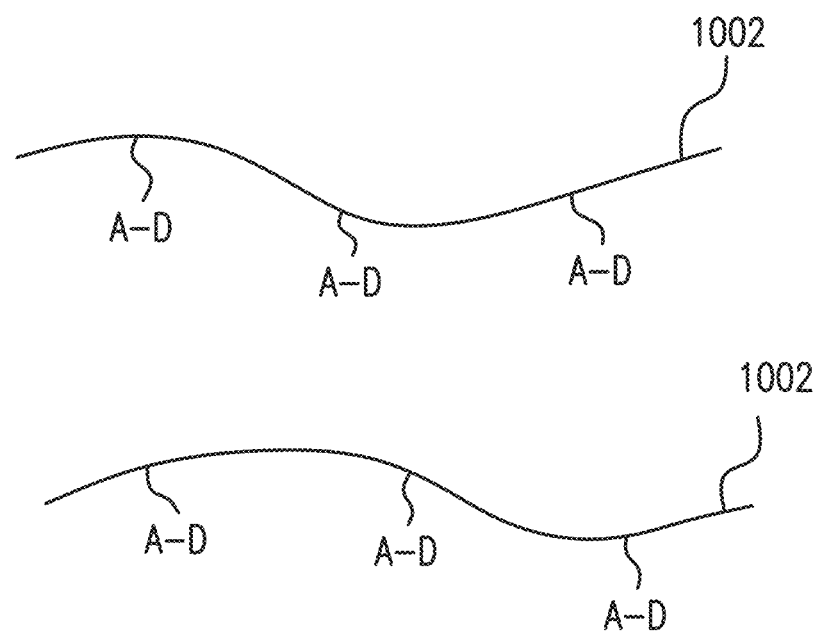

In some non-limiting embodiments, as shown in FIGS. 10-12, the indicator element 106 may include one or more polymer backbones 1002. In some non-limiting embodiments, the polymer backbones 1002 may be polymer chains.

In some embodiments, as shown in FIGS. 10 and 11, the indicator element 106 may include one or more analyte indicator molecules A and one or more degradation indicator molecules D. In some embodiments, as shown in FIGS. 10 and 11, the analyte indicator molecules A and degradation indicator molecules D may be monomers polymerized individually to a polymer backbone 1002. In some non-limiting embodiments, the indicator element 106 may include an equal number of analyte indicator molecules A and degradation indicator molecules D (see FIG. 10) or a different number of analyte indicator molecules A and degradation indicator molecules D (see FIG. 11). In some embodiments, there may be a ratio of analyte indicator molecules A to degradation indicator molecules D, such as, for example and without limitation, 1:1 as shown in FIG. 10, 2:1 as shown in FIG. 11, 1:2, 3:1, 5:1, 10:1, etc.

In some alternative embodiments, as shown in FIG. 12, one or more degradation indicator molecules D may be chemically bonded to an analyte indicator molecule A (e.g., via a covalent bond), and the analyte indicator molecule A may be chemically bonded to a polymer backbone 1002. In one non-limiting alternative embodiment, the analyte indicator molecules A and degradation indicator molecules D may be monomers, and the analyte indicator molecules A may be polymerized to the polymer backbone 1002. In some other alternative embodiments, one or more analyte indicator molecules A may be chemically bonded to a degradation indicator molecules D, and the degradation indicator molecule D may be chemically bonded to a polymer backbone 1002. In one non-limiting alternative embodiment, the analyte indicator molecules A and degradation indicator molecules D may be monomers, and the degradation indicator molecules D may be polymerized to the polymer backbone 1002.

In some embodiments, the analyte sensor 100 may measure changes to the analyte indicator 207 indirectly using the degradation indicator 209, which may by sensitive to degradation by reactive oxygen species (ROS) but not sensitive to the analyte. In some embodiments, the degradation indicator 207 may have one or more optical properties that change with extent of oxidation and may be used as a reference dye for measuring and correcting for extent of oxidation of the analyte indicator. In some embodiments, the extent to which the degradation indicator 209 has degraded may correspond to the extent to which the analyte indicator 207 has degraded. For example, in some non-limiting embodiments, the extent to which the degradation indicator 209 has degraded may be proportional to the extent to which the analyte indicator 207 has degraded. In some non-limiting embodiments, the extent to which the analyte indicator 207 has degraded may be calculated based on the extent to which the degradation indicator 209 has degraded. In some embodiments, the analyte monitoring system 50 may correct for changes in the analyte indicator 207 using an empiric correlation established through laboratory testing.

In some embodiments, as shown in FIG. 2, the analyte sensor 100 may include one or more first light sources 108 that emit first excitation light 329 over a range of wavelengths that interact with the analyte indicator 207 in the indicator element 106. In some non-limiting embodiments, the first excitation light 329 may be ultraviolet (UV) light. In some embodiments, the analyte sensor 100 may include one or more light sources 227 that emit second excitation light 330 over a range of wavelengths that interact with the degradation indicator 209 in the indicator element 106. In some non-limiting embodiments, the second excitation light 330 may be blue light.

In some embodiments, as shown in FIG. 2, the analyte sensor 100 may also include one or more photodetectors 224, 226, 228 (e.g., photodiodes, phototransistors, photoresistors, or other photosensitive elements). In some embodiments, the analyte sensor 100 may include one or more signal photodetectors 224 sensitive to first emission light 331 (e.g., fluorescent light) emitted by the analyte indicator 207 of the indicator element 106 such that a signal generated by a photodetector 224 in response thereto that is indicative of the level of first emission light 331 of the analyte indicator 207 and, thus, the amount of analyte of interest (e.g., glucose). In some non-limiting embodiments, the analyte sensor 100 may include one or more reference photodetectors 226 may be sensitive to first excitation light 329 that may be reflected from the indicator element 106. In some embodiments, the analyte sensor 100 may include one or more degradation photodetectors 228 sensitive to second emission light 332 (e.g., fluorescent light) emitted by the degradation indicator 209 of the indicator element 106 such that a signal generated by a photodetector 228 in response thereto that is indicative of the level of second emission light 332 of the degradation indicator 209 and, thus, the amount of degradation (e.g., oxidation). In some non-limiting embodiments, the one or more signal photodetectors 224 may be sensitive to second excitation light 330 that may be reflected from the indicator element 106. In this way, the one or more signal photodetectors 224 may act as reference photodetectors when the one or more light sources 227 are emitting second excitation light 330.

In some embodiments, the first excitation light 329 may be over a first wavelength range, and the second excitation light 330 over a second wavelength range, which may different than the first wavelength range. In some non-limiting embodiments, the first and second wavelength ranges do not overlap, but this not required, and, in some alternative embodiments, the first and second wavelength ranges may overlap. In some embodiments, the first emission light 331 may be over a third wavelength range, and the second emission light 332 may be over a fourth wavelength range, which may be different than the third wavelength range. In some non-limiting embodiments, the third and fourth wavelength ranges do not overlap, but this is not required, and, in some alternative embodiments, the third and fourth wavelength ranges may overlap. In some embodiments, the first and third wavelength ranges may be different. In some non-limiting embodiments, the first and third wavelength ranges do not overlap, but this is not required, and, in some alternative embodiments, the first and third wavelength ranges may overlap. In some embodiments, the second and fourth wavelength ranges may be different. In some non-limiting embodiments, the second and fourth wavelength ranges do not overlap, but this is not required, and, in some alternative embodiments, the second and fourth wavelength ranges may overlap. In some non-limiting embodiments, the second and third wavelength ranges may overlap.

In some embodiments, one or more of the photodetectors 224, 226, 228 may be covered by one or more filters that allow only a certain subset of wavelengths of light to pass through and reflect (or absorb) the remaining wavelengths. In some non-limiting embodiments, one or more filters on the one or more signal photodetectors 224 may allow only a subset of wavelengths corresponding to first emission light 331 and/or the reflected second excitation light 330. In some non-limiting embodiments, one or more filters on the one or more reference photodetectors 226 may allow only a subset of wavelengths corresponding to the reflected first excitation light 329. In some non-limiting embodiments, one or more filters on the one or more degradation photodetectors 228 may allow only a subset of wavelengths corresponding to second emission light 332.

Figure 5:
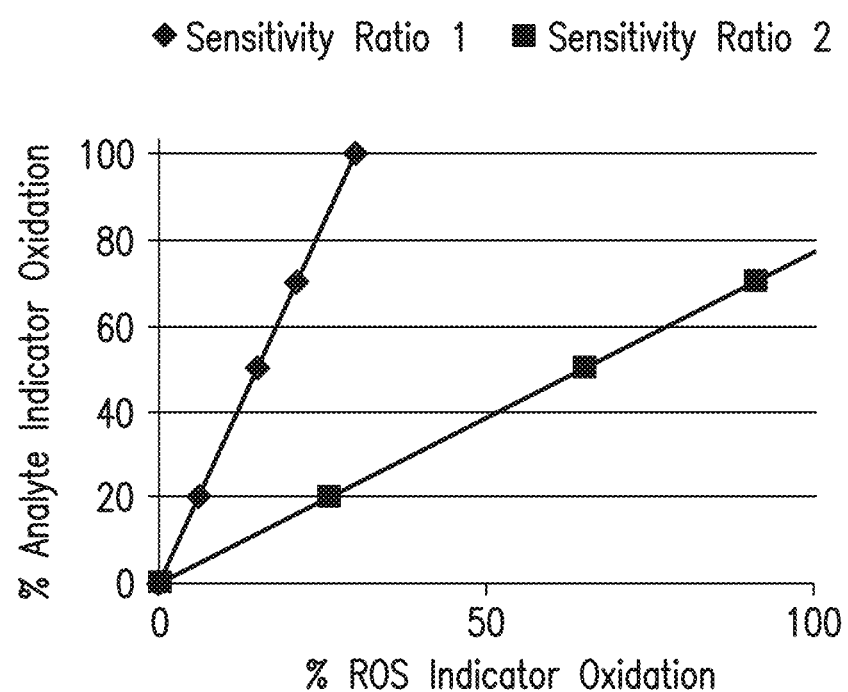
FIG. 5 is a chart illustrating non-limiting examples of sensitivity ratios correlating an analyte indicator to degradation indicators embodying aspects of the present invention.

In some embodiments, the degradation indicator 209 may be used as a reference dye for measuring and correcting for extent of oxidation of the analyte indicator 207. In some embodiments, the analyte monitoring system 50 may correct for changes in the analyte indicator 207 using an empiric correlation established through laboratory testing. FIG. 5 is a chart illustrating non-limiting examples of sensitivity ratios correlating an analyte indicator 207 to a degradation indicator 209. In some embodiments, as shown by the sensitivity ratio 1 in FIG. 5, the degradation indicator 209 may be more sensitive to oxidation than the analyte indicator 207. However, this is not required, and, in some alternative embodiments, as shown by the sensitivity ratio 2 in FIG. 5, the degradation indicator 207 may be less sensitive to oxidation than the analyte indicator 207. In some other alternative embodiments, the degradation indicator 209 and analyte indicator 207 may be equally sensitive to oxidation.

In some embodiments, the substrate 112 may be a circuit board (e.g., a printed circuit board (PCB) or flexible PCB) on which one or more of the circuit components 111 (e.g., analog and/or digital circuit components) may be mounted or otherwise attached. However, in some alternative embodiments, the substrate 112 may be a semiconductor substrate having one or more of the circuit components 111 fabricated therein. For instance, the fabricated circuit components may include analog and/or digital circuitry. Also, in some embodiments in which the substrate 112 is a semiconductor substrate, in addition to the circuit components fabricated in the semiconductor substrate, circuit components may be mounted or otherwise attached to the semiconductor substrate. In other words, in some semiconductor substrate embodiments, a portion or all of the circuit components 111, which may include discrete circuit elements, an integrated circuit (e.g., an application specific integrated circuit (ASIC)) and/or other electronic components (e.g., a non-volatile memory), may be fabricated in the semiconductor substrate with the remainder of the circuit components 111 is secured to the semiconductor substrate, which may provide communication paths between the various secured components.

In some embodiments, the analyte sensor 100 may include one or more light sources 108, 227, and one or more of the light sources 108, 227 may be mounted on or fabricated within in the substrate 112. In some embodiments, the analyte sensor 100 may include one or more photodetectors 224, 226, 228, and one or more of the photodetectors 224, 226, 228 may be mounted on or fabricated in the substrate 112. In some non-limiting embodiments, one or more light sources 108, 227 may be mounted on the substrate 112, one or more photodetectors may be fabricated within the substrate 112, and all or a portion of the circuit components 111 may be fabricated within the substrate 112.

In some embodiments, the one or more of the indicator element 106, light source(s) 108, 227, photodetectors 224, 226, 228, circuit components 111, and substrate 112 of the analyte sensor 100 may include some or all of the features described in one or more of U.S. application Ser. No. 13/761,839, filed on Feb. 7, 2013, U.S. application Ser. No. 13/937,871, filed on Jul. 9, 2013, U.S. application Ser. No. 13/650,016, filed on Oct. 11, 2012, and U.S. application Ser. No. 14/142,017, filed on Dec. 27, 2013, all of which are incorporated by reference in their entireties. Similarly, the structure, function, and/or features of the sensor housing 102, analyte sensor 100, and/or transceiver 101 may be as described in one or more of U.S. application Ser. Nos. 13/761,839, 13/937,871, 13/650,016, and 14/142,017. For instance, the sensor housing 102 may have one or more hydrophobic, hydrophilic, opaque, and/or immune response blocking membranes or layers on the exterior thereof.

Although in some embodiments, as illustrated in FIG. 1, the analyte sensor 100 may be a fully implantable sensor, this is not required, and, in some alternative embodiments, the analyte sensor 100 may be a transcutaneous sensing system having a wired connection to the transceiver 101. For example, in some alternative embodiments, the analyte sensor 100 may be located in or on a transcutaneous needle (e.g., at the tip thereof). In these embodiments, instead of wirelessly communicating using inductive elements 103 and 114, the analyte sensor 100 and transceiver 101 may communicate using one or more wires connected between the transceiver 101 and the transceiver transcutaneous needle that includes the analyte sensor 100. For another example, in some alternative embodiments, the analyte sensor 100 may be located in a catheter (e.g., for intravenous blood glucose monitoring) and may communicate (wirelessly or using wires) with the transceiver 101.

In some embodiments, the analyte sensor 100 may include a transceiver interface device. In some embodiments, the transceiver interface device may include the antenna (e.g., inductive element 114) of the analyte sensor 100. In some of the transcutaneous embodiments where there exists a wired connection between the analyte sensor 100 and the transceiver 101, the transceiver interface device may include the wired connection.

Figure 6:
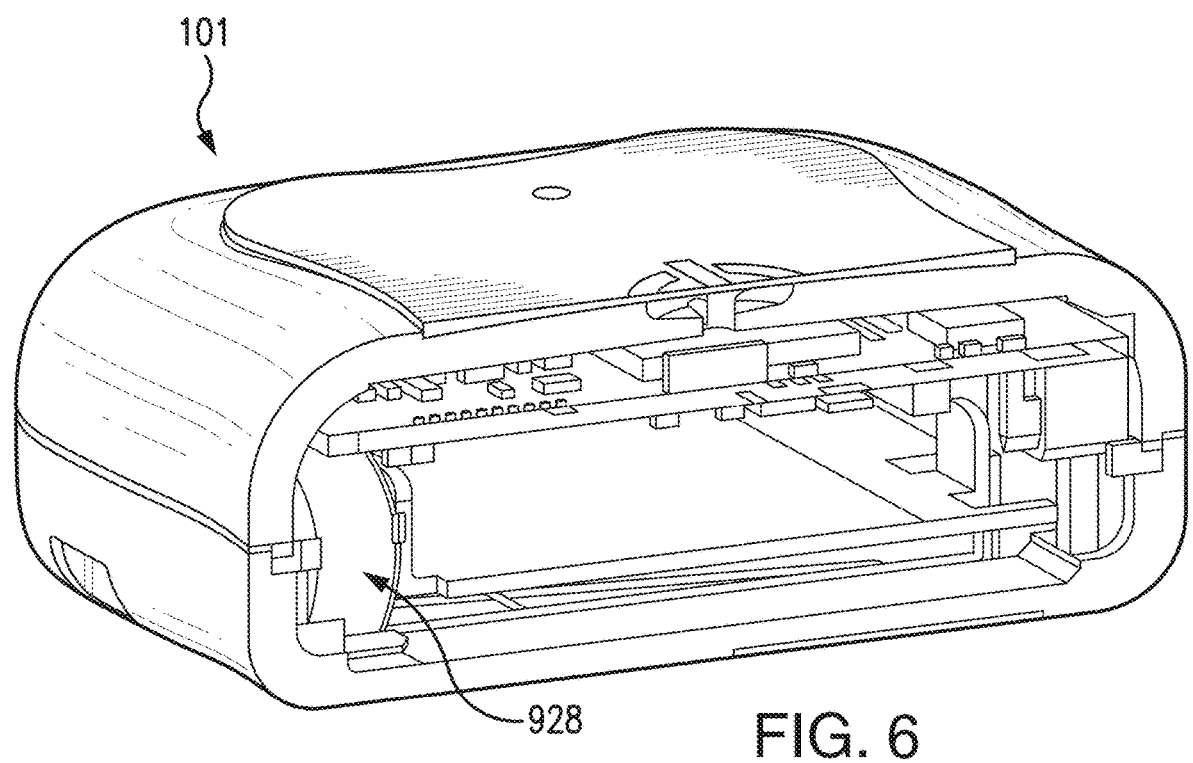
FIG. 6 is cross-sectional, perspective view of a transceiver embodying aspects of the invention.

FIGS. 6 and 7 are cross-sectional and exploded views, respectively, of a non-limiting embodiment of the transceiver 101, which may be included in the analyte monitoring system 50 illustrated in FIG. 1. As illustrated in FIG. 7, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 6 and 7, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 8:
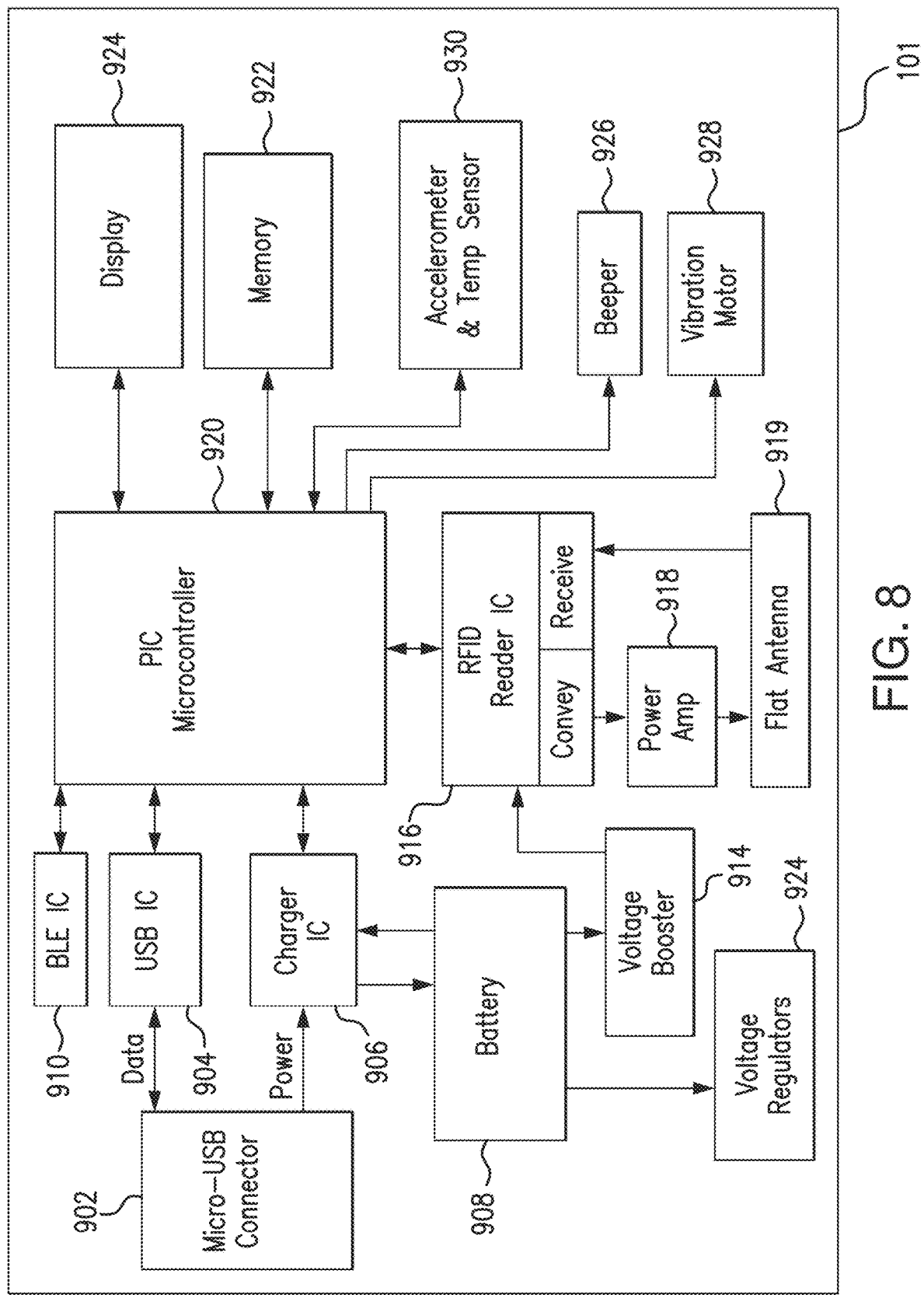
FIG. 8 is a schematic view illustrating a transceiver embodying aspects of the present invention.

FIG. 8 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 107 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 107 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 107 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 107. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

In some embodiments, the transceiver 101 may include a peripheral interface controller (PIC) controller 920 and memory 922 (e.g., Flash memory), which may be non-volatile and/or capable of being electronically erased and/or rewritten. The PIC controller 920 may control the overall operation of the transceiver 101. For example, the PIC controller 920 may control the connector IC 904 or wireless communication IC 910 to transmit data via wired or wireless communication and/or control the RFID reader IC 916 to convey data via the inductive element 103. The PIC controller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC controller 920 may control to display data (e.g., analyte concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC controller 920.

Figure 9:
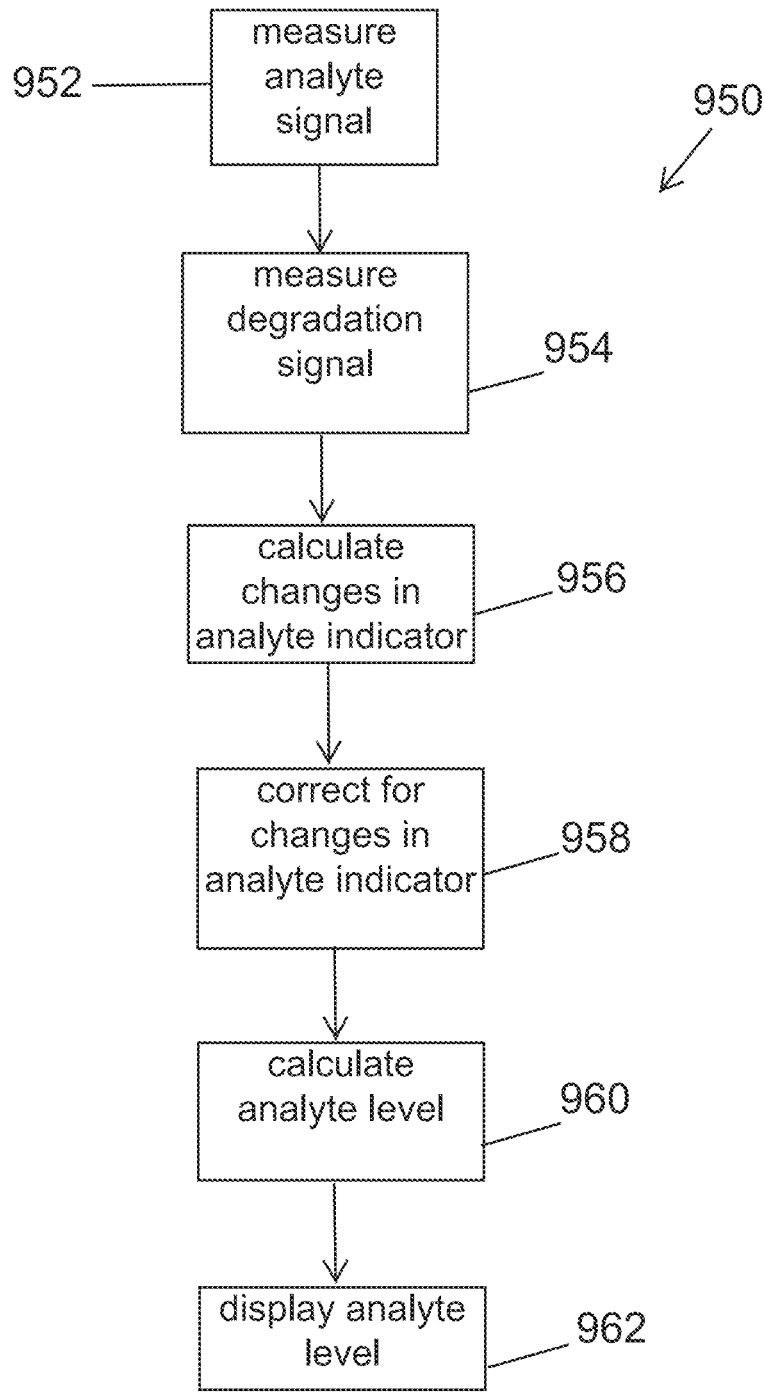
FIG. 9 is a flow chart illustrating a process for detecting and correcting for changes to an analyte indicator embodying aspects of the present invention.

FIG. 9 illustrates non-limiting embodiment of an analyte monitoring process 950 that may be performed by the analyte monitoring system 50. In some embodiments, the process 950 may detect and correct for changes to the analyte indicator 207. In some embodiments, the process 950 may include a step 952 in which the analyte monitoring system 50 measures an analyte signal. In some embodiments, the step 952 may include the transceiver 101 conveying an analyte measurement command to the analyte sensor 100. In some embodiments, the step 952 may include the analyte sensor 100, in response to receiving and decoding the analyte measurement command, using the first light source 108 to emit first excitation light 329 to the indicator element 106. The analyte indicator 207 of the indicator element 106 may receive the first excitation light 329 and emit first emission light 331. The signal photodetector 224 may receive the first emission light 331 and generate an analyte measurement signal based on the amount of first emission light 331 received by the signal photodetector 224. In some embodiments, the step 952 may include the analyte sensor 100 using the reference photodetector 226 to receive first excitation light 329 that was reflected from the indicator element 106 and generate a reference signal indicative of the amount of reflected first excitation light 329 received by the reference photodetector 226.

In some embodiments, the process 950 may include a step 954 in which the analyte monitoring system 50 measures a degradation signal. In some embodiments, the step 954 may include the transceiver 101 conveying a degradation measurement command to the analyte sensor 100. In some embodiments, the step 954 may include the analyte sensor 100, in response to receiving and decoding the degradation measurement command, using the second light source 227 to emit second excitation light 330 to the indicator element 106. The degradation indicator 209 of the indicator element 106 may receive the second excitation light 330 and emit second emission light 332. The degradation photodetector 228 may receive the second emission light 332 and generate a degradation measurement signal based on the amount of second emission light 332 received by the degradation photodetector 228. In some embodiments, the step 954 may include the analyte sensor 100 using the signal photodetector 224 to receive second excitation light 330 that was reflected from the indicator element 106 and generate a reference signal indicative of the amount of reflected second excitation light 330 received by the signal photodetector 224.

In some alternative embodiments, the step 954 may not include conveying a degradation measurement command to the analyte sensor 100, and the analyte sensor 100 may use the second light source 227 to emit the second excitation light 330 to the indicator element 106 in response to receiving and decoding an analyte measurement command (instead of in response to receiving and decoding a degradation measurement command). In some alternative embodiments, steps 952 and 954 may be performed simultaneously, and the analyte sensor 100 may use the first and second light sources 108, 227 to emit simultaneously the first and second excitation lights 329, 330 to the indicator element 106. In some alternative embodiments, step 954 may be performed before step 952.

In some embodiments, the process 950 may include a step 956 in which the analyte monitoring system 50 calculates changes in the analyte indicator 207. In some embodiments, the step 956 may include the transceiver 101 receiving sensor data from the analyte sensor 100. In some embodiments, the sensor data may include one or more of an analyte measurement, a first reference measurement, a degradation measurement, a second reference measurement, and a temperature measurement. In some embodiments, the analyte measurement may correspond to the amount of first emission light 331 received by the signal photodetector 224, the first reference measurement may correspond to the amount of reflected first excitation light 329 received by the reference photodetector 226, the degradation measurement may correspond to the amount of second emission light 332 received by the degradation photodetector 228, and the second reference measurement may correspond to the amount of reflected second excitation light 330 received by the signal photodetector 224. In some alternative embodiments, one or more of the analyte measurement and the first reference measurement may be received during step 952, and one or more of the degradation measurement and the second reference measurement may be received during step 954.

In some embodiments, the step 956 may include the transceiver 101 (e.g., the microcontroller 910 of the transceiver 101) determining the extent that the analyte indicator 207 has degraded based at least on the received degradation measurement. In some non-limiting embodiments, the step 956 may include the transceiver 101 determining (i) the extent that the degradation indicator 209 has been degraded based on the received degradation measurement and (ii) the extent that the analyte indicator 207 has been degraded based on the determined extent to which the degradation indicator 209 has been degraded. In some non-limiting embodiments, the transceiver 101 may additionally or alternatively use one or more previous degradation measurements and/or one or more previous determinations of the extent to which the degradation indicator 209 has degraded to determine the extent to which the analyte indicator 207 has degraded.

In some embodiments, the process 950 may include a step 958 in which the analyte monitoring system 50 corrects for the calculated changes to the analyte indicator 207. In some non-limiting embodiments, the transceiver 101 (e.g., the microcontroller 910 of the transceiver 101) may correct for the calculated changes to the analyte indicator 207 by adjusting the conversion function used to calculate an analyte level based on an analyte measurement. In some embodiments, adjusting the conversion function may include adjusting one or more parameters of the conversion function. In some embodiments, in step 958, the transceiver 101 may additionally or alternatively adjust the conversion function based on the first reference measurement, which may be indicative of in-vivo hydration of the indicator element 106 and/or wound healing kinetics. In some embodiments, in step 958, the transceiver 101 may additionally or alternatively adjust the conversion function based on the second reference measurement, which may be a measurement of the opacity of the indicator element 106 in the wavelength range of the first emission light 331.

In some embodiments, the process 950 may include a step 960 in which the analyte monitoring system 50 calculates an analyte level (e.g., an analyte concentration). In some embodiments, in step 960, the transceiver 101 (e.g., the microcontroller 910 of the transceiver 101) may calculate the analyte level using at least the adjusted conversion function and the analyte measurement. In some embodiments, the transceiver 101 may additionally use the temperature measurement to calculate the analyte level.

In some embodiments, the process 950 may include a step 962 in which the analyte monitoring system 50 displays the calculated analyte level. In some embodiments, in step 962, the transceiver 101 may display the analyte level on the display 924. In some embodiments, in step 962, the transceiver 101 may additionally or alternatively convey the calculated analyte level to the display device 107, and the display device 107 may additionally or alternatively convey the calculated analyte level.

EXAMPLE

Compound A was copolymerized with an indicator molecule onto a hydrogel. Methods of copolymerizing are described in U.S. Pat. No. 7,060,503 (Colvin) and U.S. Pat. No. 9,778,190 (Huffstetler et al.), which are incorporated by reference in their entireties.

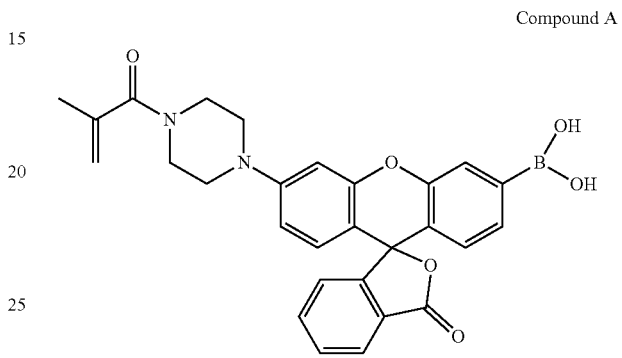

Compound A

Figure 14B:
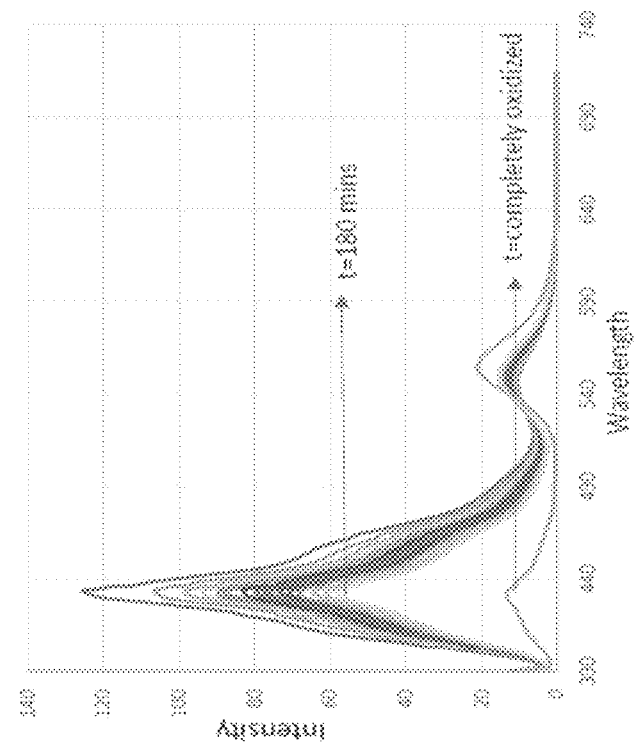
FIGS. 14A and 14B show fluorimeter readings demonstrating decrease in fluorescence intensity of indicator molecule (excitation wavelength 380 nm) at 2 mM glucose and 50 uM hydrogen peroxide with simultaneous increase in the fluorescence intensity of Compound A (excitation wavelength 470 nm) at a 1:1 ratio of indicator molecule:Compound A demonstrating the use of Compound A as a copolymerizable reference dye.
Figure 14A:
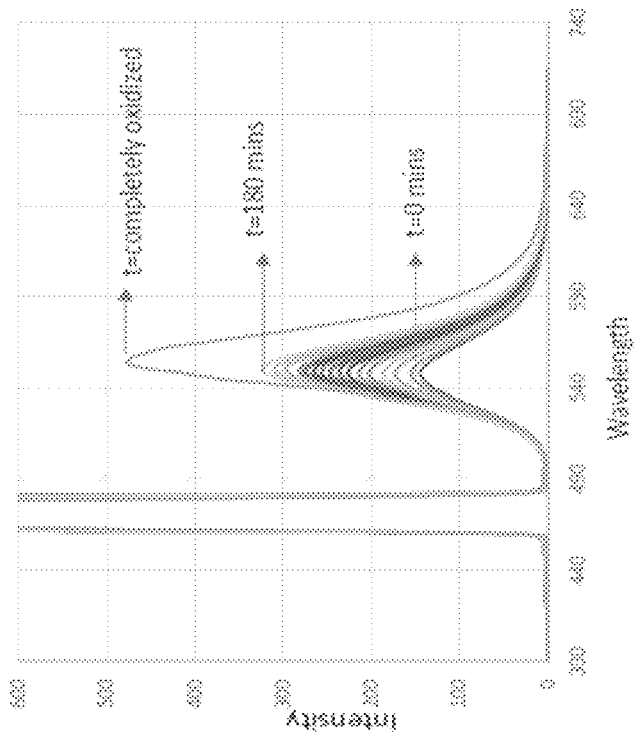

Initial characterization followed by subsequent oxidation test helped in understanding the degradation kinetics of both the reference dye (Compound A) and the indicator as shown in FIGS. 14A and 14B. Initial fluorimeter work was performed with a 1:1 ratio of indicator (TFM):Compound A demonstrating the use of Compound A as a copolymerizable reference dye. The plots in FIG. 14A and FIG. 14B demonstrate decreases in fluorescence intensity of indicator molecule (excitation wavelength 380 nm) at 2 mM glucose and 50 uM hydrogen peroxide with simultaneous increase in the fluorescence intensity of Compound A (excitation wavelength 470 nm). TFM has a chemical name of 9-[N-[6-(4,4,5,5,-tetramethyl-1,3,2-dioxaborolano)-3-(trifluoromethyl)benzyl]-N-[3-(methacrylamido)propylamino]methyl]-10-[N-[6-(4,4,5,5,-tetramethyl-1,3,2-dioxaborolano)-3-(trifluoromethyl)benzyl]-N-[2-(carboxyethyl)amino]methyl]anthracene sodium salt.

An in vivo study was performed in 18 female guinea pigs using mock sensors having a 1:1 ratio of the copolymerized indicator:Compound A in a hydrogel thereon were implanted into the guinea pigs to assess performance of Compound A in response to in vivo oxidation and its correlation to degradation of the indicator molecule. Implantation was executed subcutaneously in the back of each guinea pig (2 samples per guinea pig) with the Senseonics implant tool kit according to the implant training file. The subjects were divided into three groups of explant time points, which were at day 30, 60 and 90. Once the samples were explanted, they were washed and disinfected using ENZOL® enzymatic detergent and glutaraldehyde solution. The explanted samples were then analyzed by fluorimetry to evaluate fluorescence intensity change in Compound A and to correlate % increase in Compound A intensity to % modulation loss in the indicator.

Figure 13:
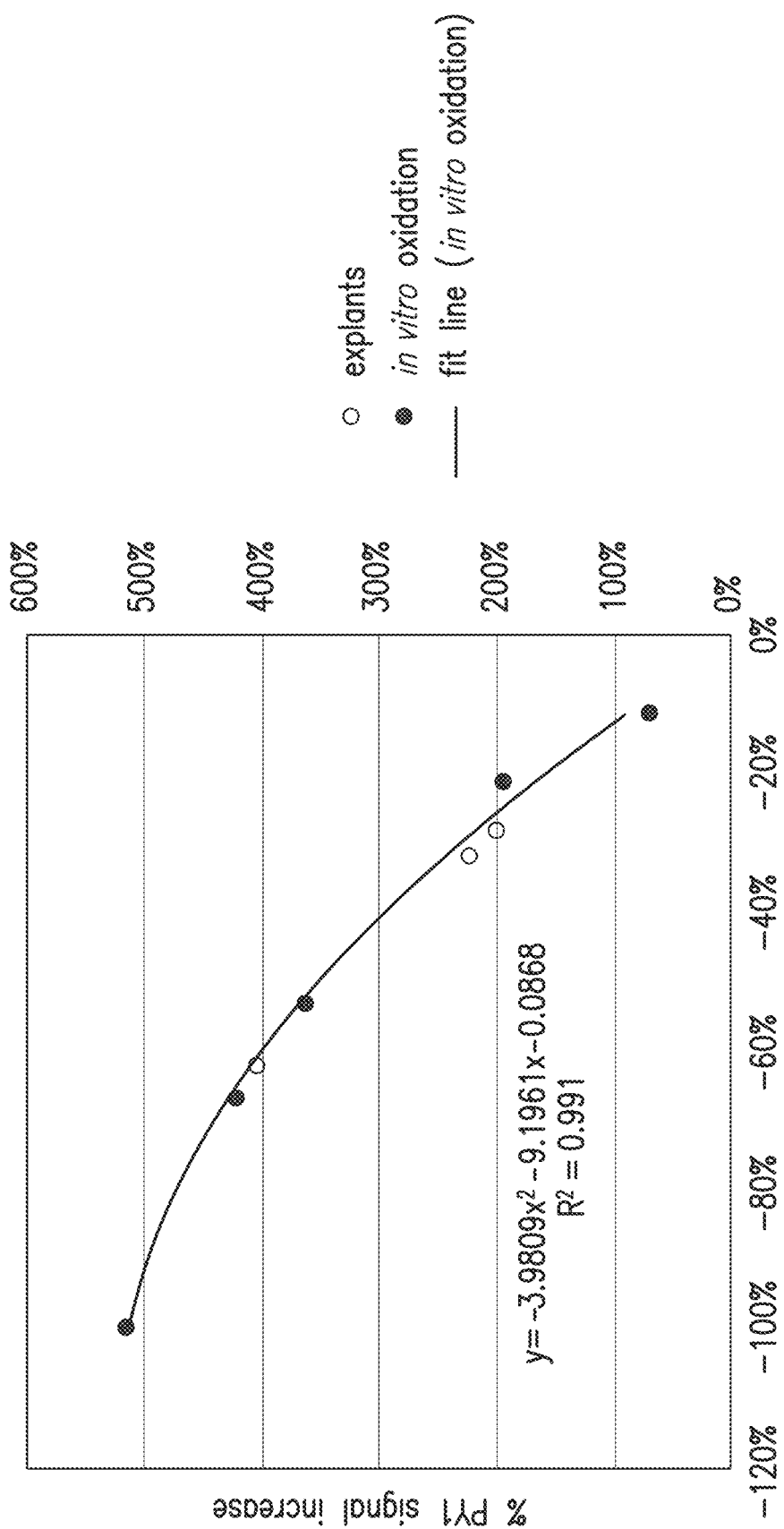
FIG. 13 is a graph illustrating a correlation plot of the rates of degradation of the indicator and the reference dyes according to one non-limiting embodiment of the invention.

An in vitro study was performed as follows: An initial 0-18 modulations were done prior to oxidation test to collect the initial modulation data. A known concentration of hydrogen peroxide was used to deliberately oxidize the sensor partially. After partial oxidation, the 0-18 modulations were performed again to collect the modulation data and record the loss in modulation. This procedure was repeated for 3-5 cycles where the same sensor undergoes further partial oxidation and at each oxidized step a 0-18 modulation data was collected. A correlation plot of the rates of degradation of both indicator and the reference dye is shown in FIG. 13.

In explant analysis of the samples, the samples showed a strong correlation between the in vitro and in vivo oxidized samples. This correlation is useful for determining the amount of modulation left at the signal channel by analyzing the amount of the indicator dye oxidation thereby reducing the number of calibrations that are performed.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although the embodiments of the invention in which the analyte indicator 207 and degradation indicator 209 are distributed throughout the same indicator element 106, this is not required. In some alternative embodiments, the analyte sensor 100 may include a first indicator element that includes the analyte indicator 207 and a second indicator element that includes the degradation indicator 209. In these alternative embodiments, the analyte indicator 207 and the degradation indicator 209 may be spatially separated from one another.

What is claimed is:

1. An analyte sensor for measurement of an analyte in a medium within a living animal, the analyte sensor comprising:
   an analyte indicator having a first detectable property that varies in accordance with (i) an amount or concentration of the analyte in the medium and (ii) an extent to which the analyte indicator has degraded, wherein the analyte indicator comprises analyte indicator molecules; and
   a degradation indicator having a second detectable property that varies in accordance with an extent to which the degradation indicator has degraded, wherein the degradation indicator comprises degradation indicator molecules, and the extent to which the degradation indicator has degraded corresponds to the extent to which the analyte indicator has degraded;
   wherein the degradation indicator molecules comprise a compound of formula I:

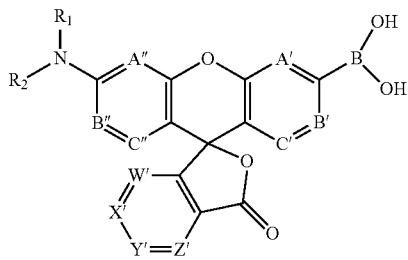

wherein A", B", C", A', B', C', W', X, Y', and Z' represent —CH, and the hydrogen of —CH may optionally and independently be substituted with an alkyl group;

wherein $R_1$ and $R_2$ are independently selected from one or more vinyl groups, alkyl vinyl groups, acrylamide groups, methacrylamide groups, or other polymerizable groups.

2. The analyte sensor of claim 1, wherein the extent to which the degradation indicator has degraded is proportional to the extent to which the analyte indicator has degraded.

3. The analyte sensor of claim 1, wherein degradation to the analyte indicator comprises reactive oxidation species (ROS)-induced oxidation, and degradation to the degradation indicator comprises ROS-induced oxidation.

4. The analyte sensor of claim 1, wherein the analyte indicator is a phenylboronic-based analyte indicator.

5. The analyte sensor of claim 1, wherein the degradation indicator is a phenylboronic-based degradation indicator.

6. The analyte sensor of claim 1, wherein a ratio of the analyte indicator molecules to the degradation indicator molecules is 1:1, 2:1, 1:2, 3:1, 5:1, or 10:1.

7. The analyte sensor of claim 1, wherein the degradation indicator comprises a fluorescent probe compound having a wavelength of excitation between about 450 nm and about 550 nm.

8. The analyte sensor of claim 7, wherein the fluorescent probe compound has a Stokes shift between about 500 nm and about 650 nm.

9. The analyte sensor of claim 8, wherein the fluorescent probe compound has a half-life of between 50 days and 150 days.

10. The analyte sensor of claim 1, wherein the second detectable property does not vary in accordance with the amount or concentration of the analyte in the medium.

11. An analyte sensor for measurement of an analyte in a medium within a living animal, the analyte sensor comprising:
   an analyte indicator having a first detectable property that varies in accordance with (i) an amount or concentration of the analyte in the medium and (ii) an extent to which the analyte indicator has degraded, wherein the analyte indicator comprises analyte indicator molecules; and
   a degradation indicator having a second detectable property that varies in accordance with an extent to which the degradation indicator has degraded, wherein the degradation indicator comprises degradation indicator molecules, and the extent to which the degradation indicator has degraded corresponds to the extent to which the analyte indicator has degraded;
   wherein the degradation indicator molecules comprise a molecule selected from the group consisting of:

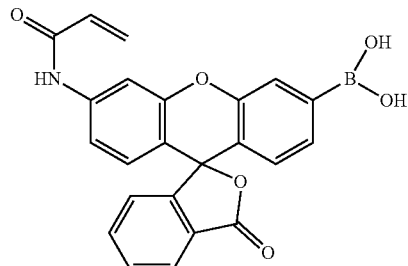

-continued

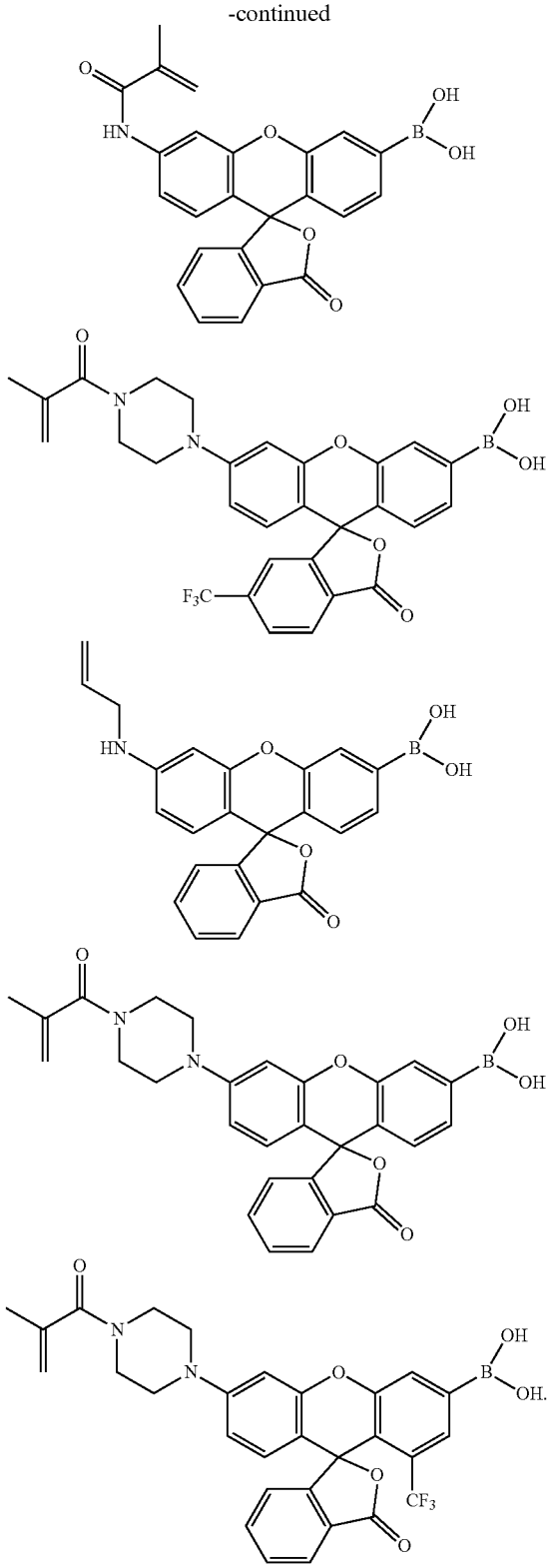

12. An analyte sensor for measurement of an analyte in a medium within a living animal, the analyte sensor comprising:

an analyte indicator having a first detectable property that varies in accordance with (i) an amount or concentration of the analyte in the medium and (ii) an extent to which the analyte indicator has degraded, wherein the analyte indicator comprises analyte indicator molecules; and a degradation indicator having a second detectable property that varies in accordance with an extent to which the degradation indicator has degraded, wherein the degradation indicator comprises degradation indicator molecules, and the extent to which the degradation indicator has degraded corresponds to the extent to which the analyte indicator has degraded;

wherein the degradation indicator molecules comprise the following molecule:

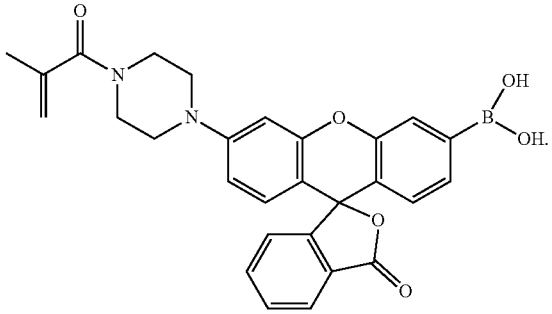 [SMILES: C=C(C)C(=O)N1CCN(c2ccc3c(c2)Oc2cc(B(O)O)ccc2C32OC(=O)c3ccccc32)CC1]

13. A method comprising:

using an analyte indicator of an analyte sensor to generate an analyte measurement indicative of an amount or concentration of an analyte in a medium, wherein the analyte indicator comprises analyte indicator molecules;

using a degradation indicator of the analyte sensor to generate a degradation measurement indicative of an extent to which the degradation indicator has degraded, wherein the degradation indicator comprises degradation indicator molecules;

calculating an extent to which the analyte indicator of the analyte sensor has degraded based at least on the degradation measurement;

adjusting a conversion function based on the calculated extent to which the analyte indicator has degraded; and calculating an analyte level using the adjusted conversion function and the analyte measurement;

wherein the degradation indicator molecules comprise a compound of formula I:

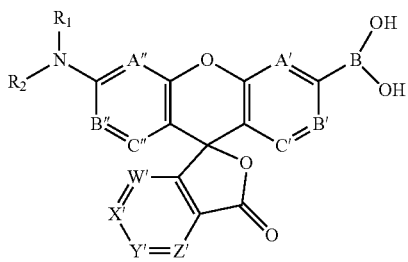

wherein A", B", C", A', B', C', W', X, Y', and Z' represent —CH, and the hydrogen of —CH may optionally and independently be substituted with an alkyl group;

wherein $R_1$ and $R_2$ are independently selected from one or more vinyl groups, alkyl vinyl groups, acrylamide groups, methacrylamide groups, or other polymerizable groups.

14. A method comprising:

using an analyte indicator of an analyte sensor to generate an analyte measurement indicative of an amount or concentration of an analyte in a medium, wherein the analyte indicator comprises analyte indicator molecules;

using a degradation indicator of the analyte sensor to generate a degradation measurement indicative of an extent to which the degradation indicator has degraded, wherein the degradation indicator comprises degradation indicator molecules;

calculating an extent to which the analyte indicator of the analyte sensor has degraded based at least on the degradation measurement;

adjusting a conversion function based on the calculated extent to which the analyte indicator has degraded; and calculating an analyte level using the adjusted conversion function and the analyte measurement;

wherein the degradation indicator molecules comprise the following molecule:

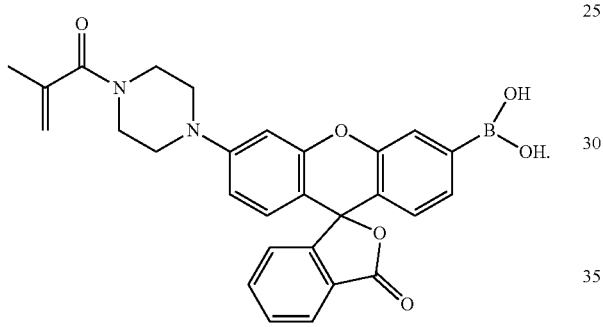

15. An analyte monitoring system comprising:

an analyte indicator having a first detectable property that varies in accordance with (i) an amount or concentration of an analyte in a medium and (ii) an extent to which the analyte indicator has degraded, wherein the analyte indicator comprises analyte indicator molecules;

a degradation indicator having a second detectable property that varies in accordance with an extent to which the degradation indicator has degraded, wherein the degradation indicator comprises degradation indicator molecules;

sensor elements configured to generate (i) an analyte measurement based on the first detectable property and (ii) a degradation measurement based on the second detectable property; and a controller configured to:

(i) calculate an extent to which the analyte indicator of the analyte sensor has degraded based at least on the degradation measurement;

(ii) adjust a conversion function based on the calculated extent to which the analyte indicator has degraded;

(iii) calculate an analyte level using the adjusted conversion function and the analyte measurement;

wherein the degradation indicator molecules comprise a compound of formula I:

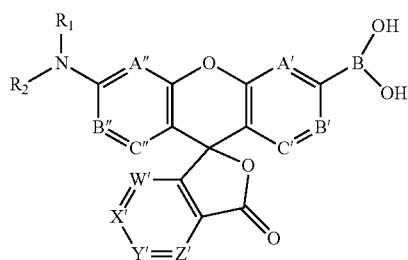

wherein A″, B″, C″, A', B', C', W', X, Y', and Z' represent —CH, and the hydrogen of —CH may optionally and independently be substituted with an alkyl group;

wherein $R_1$ and $R_2$ are independently selected from one or more vinyl groups, alkyl vinyl groups, acrylamide groups, methacrylamide groups, or other polymerizable groups.

16. The analyte monitoring system of claim 15, wherein the second detectable property does not vary in accordance with the amount or concentration of the analyte in the medium.

17. An analyte monitoring system comprising:

an analyte indicator having a first detectable property that varies in accordance with (i) an amount or concentration of an analyte in a medium and (ii) an extent to which the analyte indicator has degraded, wherein the analyte indicator comprises analyte indicator molecules;

a degradation indicator having a second detectable property that varies in accordance with an extent to which the degradation indicator has degraded, wherein the degradation indicator comprises degradation indicator molecules;

sensor elements configured to generate (i) an analyte measurement based on the first detectable property and (ii) a degradation measurement based on the second detectable property; and a controller configured to:

(iii) calculate an extent to which the analyte indicator of the analyte sensor has degraded based at least on the degradation measurement;

(iv) adjust a conversion function based on the calculated extent to which the analyte indicator has degraded;

(v) calculate an analyte level using the adjusted conversion function and the analyte measurement;

wherein the degradation indicator molecules comprise a molecule selected from the group consisting of:

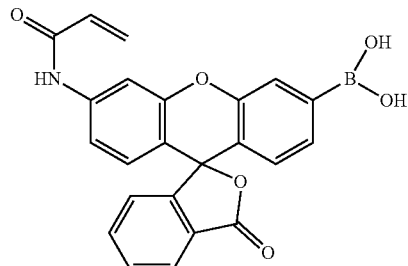

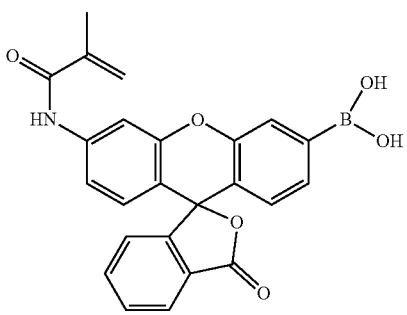

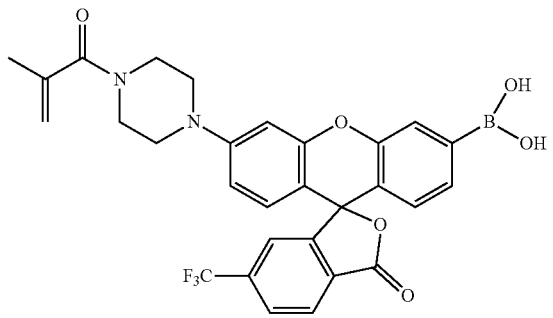

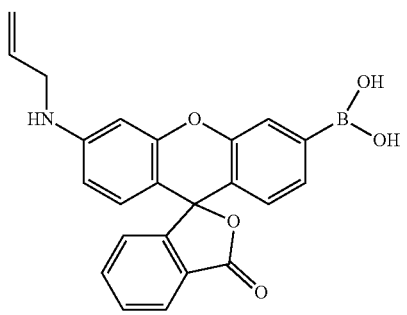

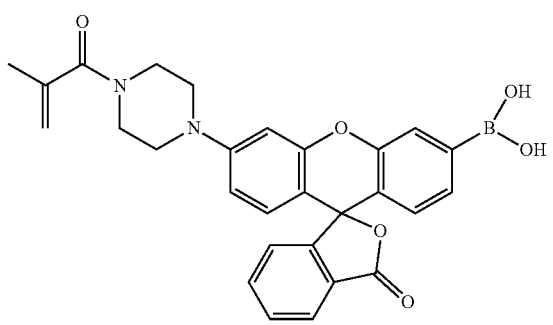

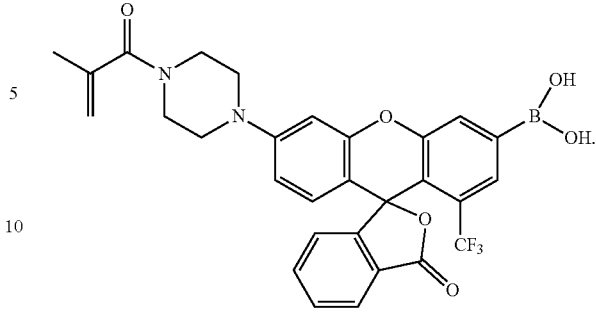

18. An analyte monitoring system comprising:
an analyte indicator having a first detectable property that varies in accordance with (i) an amount or concentration of an analyte in a medium and (ii) an extent to which the analyte indicator has degraded, wherein the analyte indicator comprises analyte indicator molecules;
a degradation indicator having a second detectable property that varies in accordance with an extent to which the degradation indicator has degraded, wherein the degradation indicator comprises degradation indicator molecules;
sensor elements configured to generate (i) an analyte measurement based on the first detectable property and (ii) a degradation measurement based on the second detectable property; and
a controller configured to:
(iii) calculate an extent to which the analyte indicator of the analyte sensor has degraded based at least on the degradation measurement;
(iv) adjust a conversion function based on the calculated extent to which the analyte indicator has degraded;
(v) calculate an analyte level using the adjusted conversion function and the analyte measurement;
wherein the degradation indicator molecules comprise the following molecule:

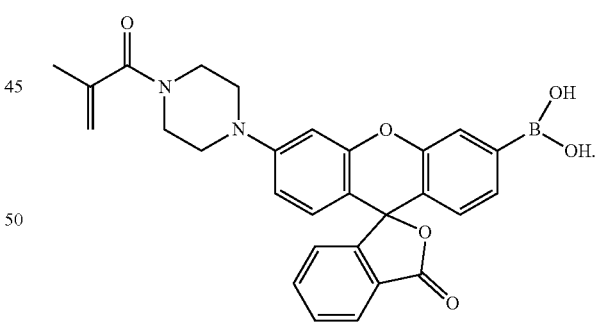

* * * * *